(12) United States Patent
Surushe et al.

(10) Patent No.: US 11,376,170 B2
(45) Date of Patent: Jul. 5, 2022

(54) FASTENING SYSTEMS COMPRISING NONWOVEN SUBSTRATES WITH HOOKS FORMED INTEGRALLY THEREON

(71) Applicant: The Procter & Gamble Company, Cincinnati, OH (US)

(72) Inventors: Abhishek Prakash Surushe, Schwalbach am Taunus (DE); Russell Andrew Hayden, New Richmond, OH (US); James David Landgrebe, Madeira, OH (US); Jeromy Thomas Raycheck, South Lebanon, OH (US); Nayda Liz Ramos Medina, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 320 days.

(21) Appl. No.: 16/545,425

(22) Filed: Aug. 20, 2019

(65) Prior Publication Data
US 2020/0060898 A1 Feb. 27, 2020

Related U.S. Application Data

(60) Provisional application No. 62/720,554, filed on Aug. 21, 2018.

(51) Int. Cl.
*A61F 13/62* (2006.01)
*A61F 13/56* (2006.01)
*A44B 18/00* (2006.01)

(52) U.S. Cl.
CPC ...... *A61F 13/5633* (2013.01); *A44B 18/0011* (2013.01); *A44B 18/0015* (2013.01); *A61F 13/625* (2013.01); *A61F 13/627* (2013.01)

(58) Field of Classification Search
CPC .............. A61F 13/5633; A61F 13/5644; A61F 13/581; A61F 13/62; A61F 13/622; A61F 13/625; A61F 13/627
See application file for complete search history.

(56) References Cited

U.S. PATENT DOCUMENTS 5,858,515 A 1/1999 Stokes
6,478,784 B1 11/2002 Johnson
(Continued)

FOREIGN PATENT DOCUMENTS

CN 1269747 A 10/2000
EP 1377214 B1 4/2005
(Continued)

OTHER PUBLICATIONS

All Office Actions; U.S. Appl. No. 16/711,478.
International Search Report, PCT/US2019/047208, dated Nov. 27, 2019, 15 pages.

*Primary Examiner* — Catharine L Anderson
(74) *Attorney, Agent, or Firm* — Sarah M. DeCristofaro

(57) ABSTRACT

A wearable article includes hook-and-loop fastening components. The hook-and-loop fastening components have a section of nonwoven web material on which an array of hooks is formed. At least some of the hooks may be integrally formed from the nonwoven material. The section of nonwoven web material may also include a section of loops material, wherein at least some of the loops may be integrally formed from the web material. The section of loops material may have a machine direction dimension of at least 20 mm and a cross direction dimension of at least 20 mm, and a surface area of at least 314 mm². The article may further include an identifiable linear path, the identifiable linear path having a width greater than 2 mm and forming an angle with the machine direction of 45 degrees or less. Any such identifiable path at least partially overlies the loops-forming bond(s), at a plurality of locations along the identifiable linear path.

13 Claims, 29 Drawing Sheets

(56) References Cited

U.S. PATENT DOCUMENTS

| | | | |
|---|---|---|---|
| 6,613,032 B2 * | 9/2003 | Ronnberg | A61F 13/64 604/385.03 |
| 6,746,434 B2 | 6/2004 | Johnson | |
| 6,945,968 B2 | 9/2005 | Svensson et al. | |
| 8,784,722 B2 | 7/2014 | Rocha | |
| 9,068,912 B2 | 6/2015 | Kline | |
| 9,138,362 B2 | 9/2015 | Popp | |
| 9,265,673 B2 | 2/2016 | Stabelfeldt | |
| 9,265,674 B2 | 2/2016 | Hancock-cooke | |
| 9,333,125 B2 | 5/2016 | Kline | |
| 9,339,425 B2 | 5/2016 | Stabelfeldt | |
| 9,468,569 B2 | 10/2016 | Hancock-cooke | |
| 9,597,237 B2 | 3/2017 | Enz | |
| 9,615,980 B2 | 4/2017 | Enz | |
| 10,798,997 B2 | 10/2020 | Rocha | |
| 2005/0101930 A1 | 5/2005 | Tachauer et al. | |
| 2009/0246770 A1 | 10/2009 | Levy | |
| 2010/0180407 A1 | 7/2010 | Rocha | |
| 2013/0131625 A1 | 5/2013 | Schlinz | |
| 2014/0000003 A1 | 1/2014 | Ashraf et al. | |
| 2014/0200543 A1 | 7/2014 | Chatterjee | |
| 2017/0065468 A1 | 3/2017 | Stabelfeldt | |
| 2017/0087034 A1 | 3/2017 | Bosser | |
| 2017/0196739 A1 * | 7/2017 | Von Jakusch | A61F 13/15756 |
| 2018/0050484 A1 * | 2/2018 | Rocha | A44B 18/0049 |
| 2018/0200125 A1 | 7/2018 | Magee | |
| 2020/0113749 A1 | 4/2020 | Surushe et al. | |

FOREIGN PATENT DOCUMENTS

| | | |
|---|---|---|
| WO | WO2009057119 A2 | 5/2009 |
| WO | WO2010085492 A1 | 7/2010 |
| WO | WO2014004023 A1 | 1/2014 |
| WO | WO2014109971 A1 | 7/2014 |
| WO | WO2016022629 A1 | 2/2016 |
| WO | WO2019018721 A1 | 1/2019 |

* cited by examiner

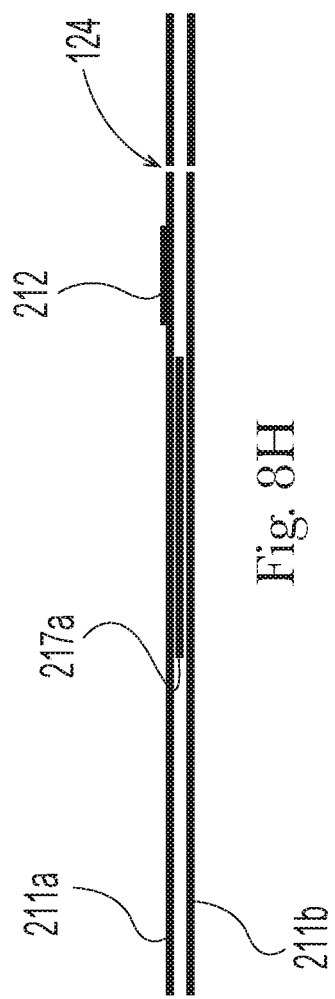

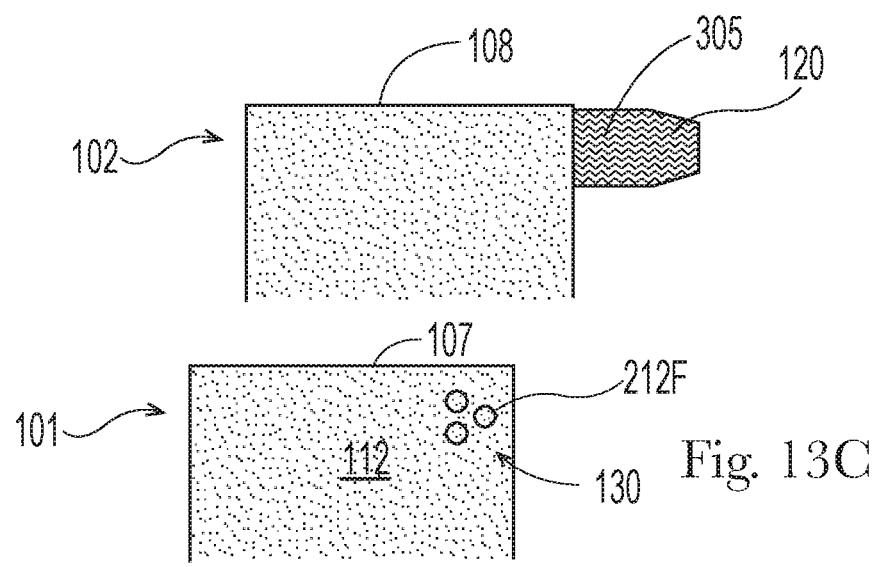
Fig. 13C
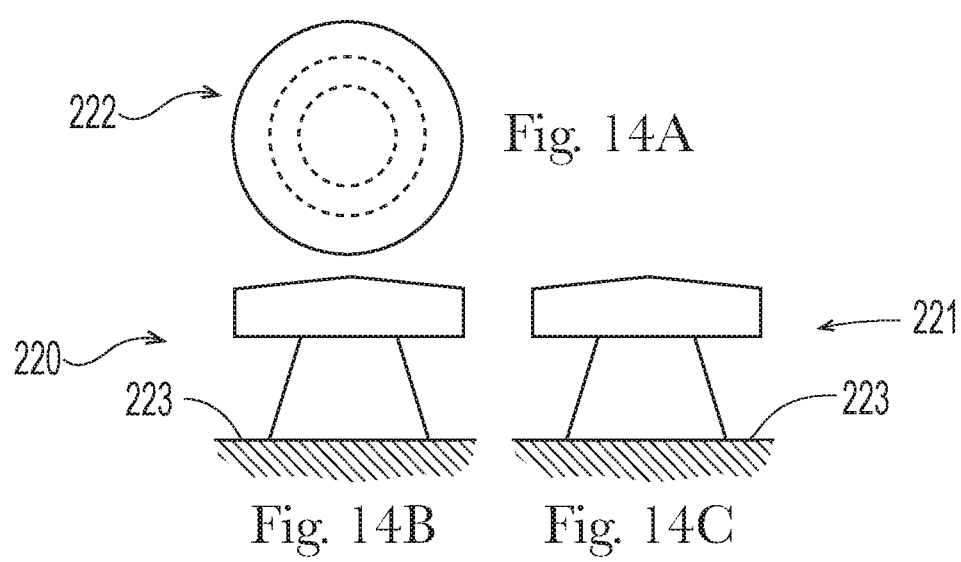
Fig. 14A
Fig. 14B    Fig. 14C

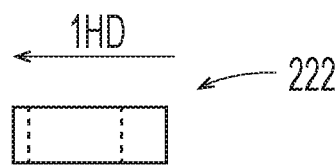
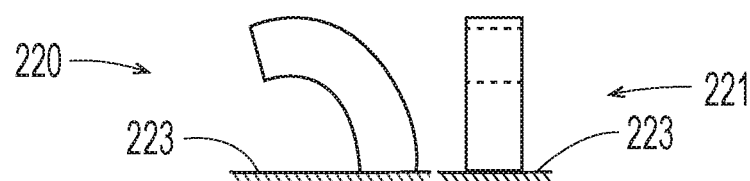
Fig. 15A
Fig. 15C
Fig. 15B
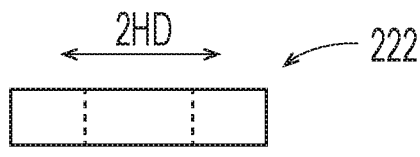
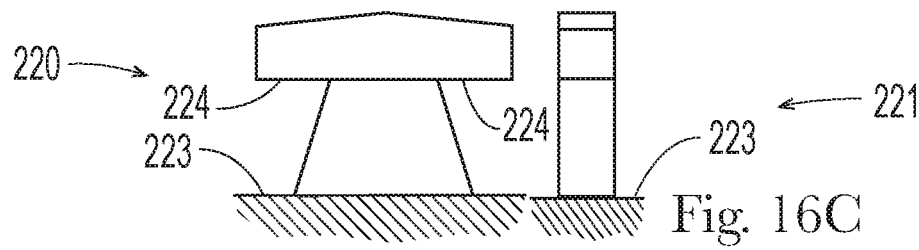
Fig. 16A
Fig. 16C
Fig. 16B

FASTENING SYSTEMS COMPRISING NONWOVEN SUBSTRATES WITH HOOKS FORMED INTEGRALLY THEREON

BACKGROUND

Hook-and-loop fastening systems have been used in a variety of applications for a number of years. Such applications have included fastening systems for wearable garments and articles, including but not limited to disposable diapers. One currently popular configuration of disposable diaper/fastening system includes an absorbent chassis having a front waist region, crotch region and rear waist region, with a pair of fastening members each extending respectively laterally from left and right longitudinal edges of the chassis in the rear waist region. In a typical configuration, each fastening member includes a patch of material bearing hooks, affixed to the wearer-facing side of the fastening member. A patch or section of cooperating loops material is typically disposed on the outward-facing side of the front waist region. In this configuration, the chassis may be wrapped through the wearer's crotch area with the back waist region placed across the wearer's lower back and buttocks and the front waist region placed across the wearer's lower belly area. The left and right fastening members may then be wrapped about the wearer's left and right hips, respectively, and fastened to the front waist region via engagement of the hooks patches with the loops material on the front waist region, thereby securing the diaper on the wearer.

Hooks of various designs for use with various types of loops material have been developed over the years, as have techniques for efficiently manufacturing hooks. Manufacturers of hooks have included the Velcro Companies (United Kingdom), 3M Company (Minnesota, USA) and Aplix (France). One technique has included heating thermoplastic resin in an extruder, extruding a base sheet and then molding and/or otherwise forming hooks into one face of the base sheet from the material thereof, while it is still soft or partially molten. Another technique has included extruding a continuous structure having a base sheet portion and a series of extruded formations extending from the base sheet portion having desired hook profiles. Following extrusion, a series of cuts through the formations are made along a direction transverse to the extrusion direction to create rows of hooks structures, without cutting through the base portion. The base sheet with rows of hooks structures is then plastically stretched along the extrusion direction, to create or enlarge separation between the rows of hooks structures. In many applications, a layer of suitable adhesive may be applied to the underside of the base material. The combination of hooks/base sheet material and adhesive may then be cut to any commercially desired size or shape, such as strips, and may be gathered, e.g., on a roll, for delivery to the purchaser/user. The purchaser/user may further cut the product to a desired size (e.g. a hooks patch) to be affixed to an article and thereby provide the hooks component of a hook-and-loop fastening system for the article.

More recently, techniques have been developed that enable formation of patterns of hooks directly on a preexisting substrate, such as a film or nonwoven. Such techniques may provide a benefit in elimination of processing and handling steps involving hooks materials and manufacture of articles with hook-and-loop fastening systems, including disposable diapers. However, it is believed that these techniques and the benefits they may provide in a variety of particular applications have not been fully developed or appreciated.

SUMMARY OF INVENTION

A wearable article may include a section of nonwoven web material having a machine direction of formation (MD). The section of nonwoven material comprises filaments of polymeric material and an array of hooks. At least some of the hooks may be integrally molded in part of the polymeric material of the filaments. The section of nonwoven material may also comprise a loops material having a plurality of loops, and at least some are integrally formed from the nonwoven material.

In some embodiments, the wearable article may be in the form of a diaper, having a chassis comprising a liquid permeable topsheet, a liquid impermeable backsheet and an absorbent core structure disposed between the topsheet and the backsheet. The diaper may include a fastening member joined to the chassis in the rear waist region and extending laterally away from the longitudinal axis, including a first fastening component disposed thereon; and a second fastening component located on the front waist region. One of both of the first and second fastening components comprises a section of nonwoven web material on which an array of hooks is formed, wherein the section of web material comprises filaments of polymeric material. The section of nonwoven web material has a machine direction of formation, and the filaments of polymeric material having a machine direction bias and are consolidated and bonded in a pattern of thermal bonds. The section of nonwoven web material may also comprise a section of loops material having a machine direction dimension of at least 20 mm, a cross direction dimension of at least 20 mm, and a surface area of at least 314 $mm^2$, and being bonded in a continuous loops-forming bond, or pattern of discrete loops-forming bonds. Any identifiable linear path along the section of loops material that has a width greater than 2 mm and forms an angle of 45 degrees or less with the machine direction (MD) at least partially overlies the loops-forming bond or bonds in the pattern, at a plurality of locations along the identifiable path. At least some of the hooks may be thermally formed at least in part of the polymeric material of the filaments such that at least part of the array is integral with the nonwoven web material.

The disclosure further includes a method for producing a fastening component material having both hook elements and loop elements, comprising the steps of:

spinning a plurality of filaments from one or more polymeric resins, and depositing the spun filaments onto a belt moving along a machine direction to form a batt of the filaments;

conveying the batt via the moving belt to a nip between one or more pairs of rollers and/or a nip between a roller and an ultrasonically vibrating surface, wherein at least one roller among one or more pairs of rollers and/or roller and ultrasonically vibrating surface comprises bonding protrusions arranged in a pattern along a surface thereof;

wherein at least one roller among one or more pairs of rollers and/or roller and ultrasonically vibrating surface comprises hooks-forming cavities arranged along a surface thereof;

consolidating the batt and bonding the filaments together in a pattern of thermal bonds via the bonding protrusions, forming a bonded nonwoven web; and forming an arrangement of hooks from polymeric material of the filaments via the hooks-forming cavities, wherein the arrangement of hooks are integral with the bonded nonwoven web.

BRIEF DESCRIPTION OF THE DRAWINGS

FIG. 8H is a schematic cross section of the section of web material shown in FIG. 7G, taken through line 8H-8H in FIG. 8G, and shown with layers separated.

FIGS. 13A-13C are schematic views of combinations of examples of front and rear waist regions of diapers with various combinations of fastening component configurations.

FIGS. 14A-14C, 15A-15C, and 16A-16C depict front, side and top views of examples of profiles of hooks protruding from a substrate.

DETAILED DESCRIPTION

Definitions

Figure 1:
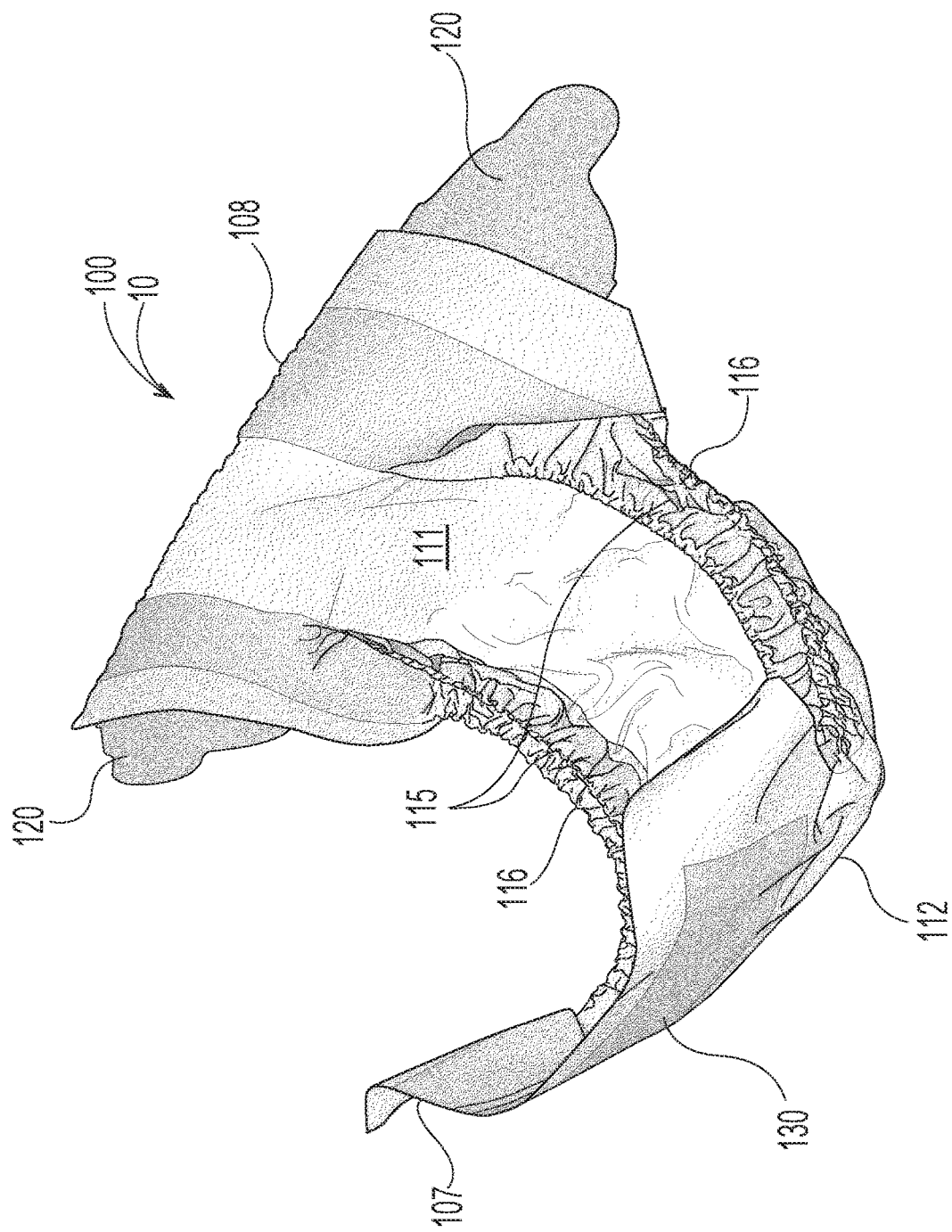
FIG. 1 is a perspective view of an example of a disposable diaper as it might appear in a relaxed condition prior to application to an infant-wearer.

"Elastic" or "elastomeric" refers to the property of a material such as a stretch laminate material that elongates, without substantial rupture or breakage, by at least 50% at a load of between 0.1 and 10 N/cm in the Hysteresis Test. Rupture or breakage having a dimension less than 5 mm in any direction is not considered substantial rupture or breakage. However, ruptures through the structure having a dimension greater than 5 mm in any direction, breaks, ruptures or tears into two or more pieces, or breaks, ruptures or tears resulting in significant structural degradation which render the material unusable for its intended purpose, are considered substantial ruptures or breakage. Further, upon release of the load, the elastic material has a set less than or equal to 20% as measured by the Hysteresis Test. For example, an elastic material that has an initial length of 25 millimeters can elongate to at least 37.5 millimeters (50% elongation) and, upon removal of the force, retract to a length of 27.5 millimeters, i.e., have a set of 2.5 millimeters (10% set), when subjected to the Hysteresis Test.

With respect to hooks, as used herein, the term "integrally molded" and variants thereof refers to hooks that are molded directly onto a substrate, partially or entirely from thermoplastic material of which the substrate is formed, via equipment having mold cavities, and equipment providing heating energy. Accordingly, integrally molded hooks and the substrate on which they are formed will have one or more thermoplastic component materials in common.

"Lateral," with respect to a diaper or components thereof, refers to the direction that is parallel to the waist edges of the diaper when it is open and laid out flat along a horizontal plane.

"Like chemistry," with respect to two polymeric compositions, means that the two compositions are capable of mixing together at a temperature of 250 deg. C. or lower, to form a single thermodynamic phase.

"Longitudinal," with respect to a diaper or components thereof, refers to the direction that is perpendicular to the waist edges of the diaper when it is open and laid out flat along a horizontal plane.

"Machine direction," with respect to manufacture of nonwoven web material, means the direction along which the web material is formed and moves through a nip between calender/bonding rolls.

"Machine direction bias," with respect to filaments forming a spunbond nonwoven web material, means that a majority of the filaments, as situated in the web material and unstretched, have lengths with machine direction vector components that are greater than their cross direction vector components.

"Cross direction," with respect to manufacture of nonwoven web material, means the direction perpendicular to the machine direction, along an x-y plane occupied by the web material.

"Outward-facing," with respect to surfaces of components of a diaper, means the surfaces that face away from the wearer's body when the diaper is worn.

"Wearer-facing," with respect to surfaces of components of a diaper, means the surfaces that face the wearer's body when the diaper is worn.

"z-direction," with respect to a web material, is the direction orthogonal to an x-y plane occupied by the web material when laid out flat.

Wearable Articles

Figure 2:
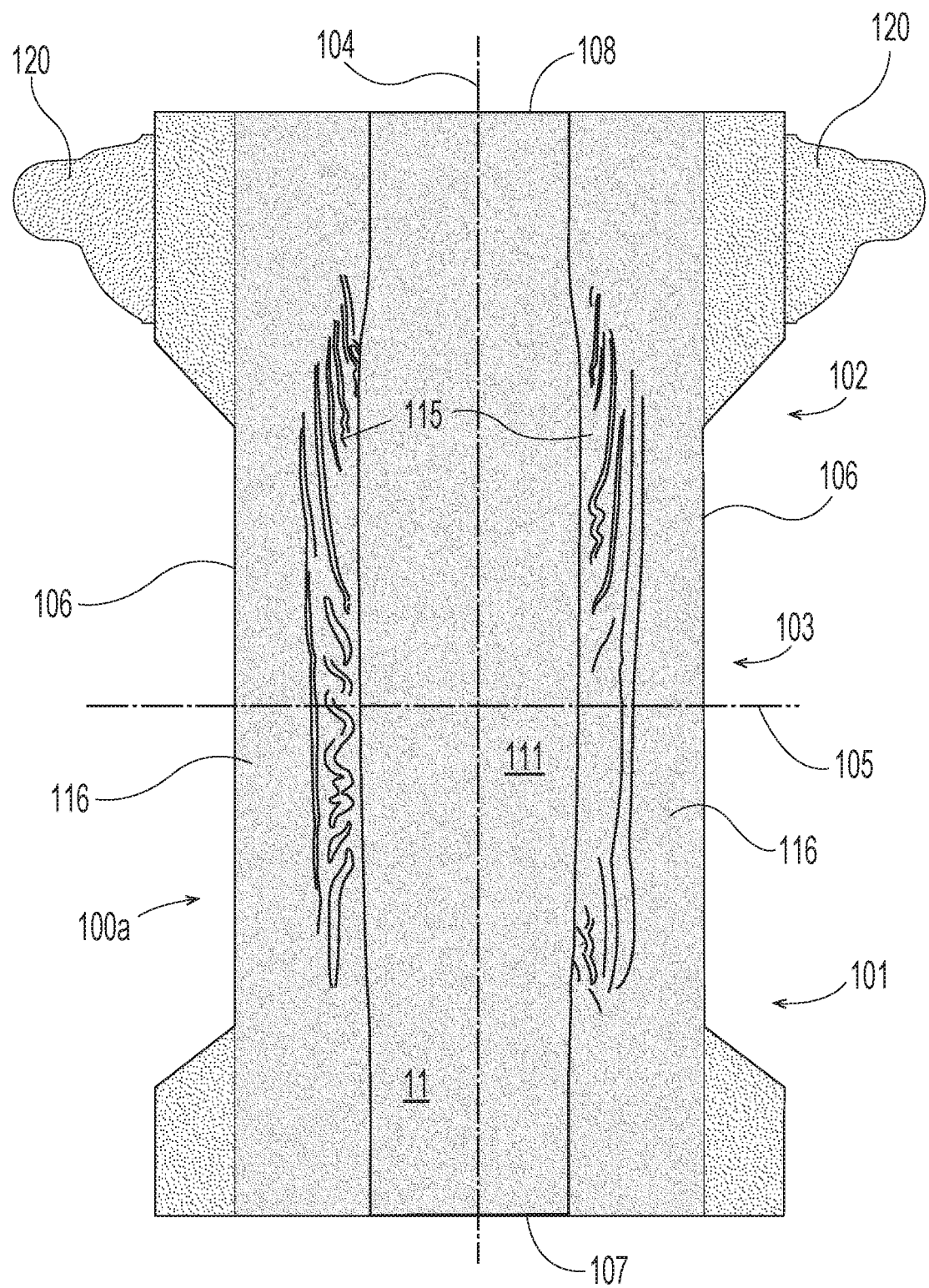
FIG. 2 is a plan view of the diaper of FIG. 1, shown extended against contraction induced by elastomeric components, to substantially the full dimensions of its non-elastic components, shown with wearer-facing surfaces facing the viewer.
Figure 3:
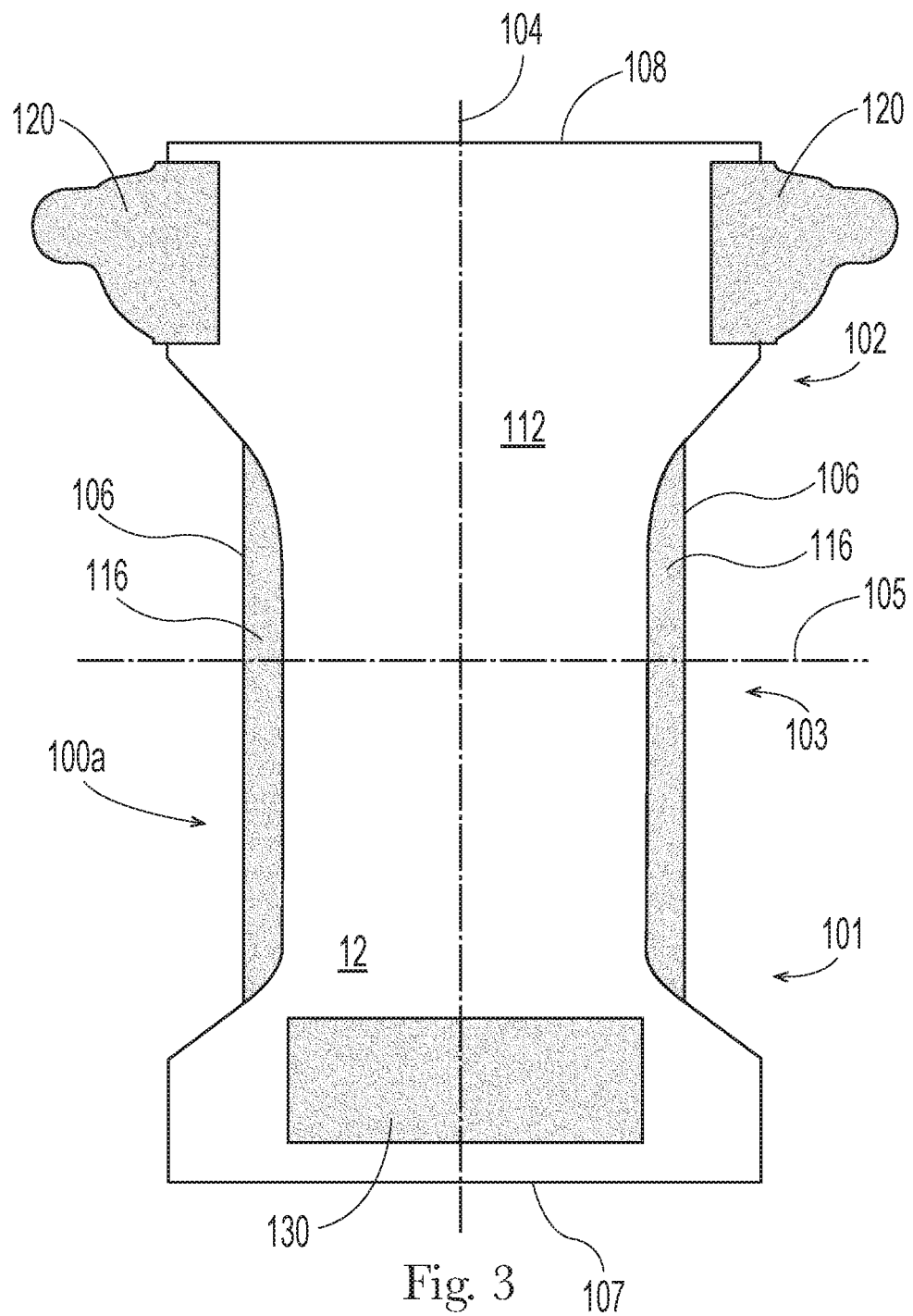
FIG. 3 is a plan view of the diaper of FIG. 1, shown extended against contraction induced by elastomeric components, to substantially the full dimensions of its non-elastic components, shown with outward-facing surfaces facing the viewer.

FIG. 1 depicts an example of a wearable article 10 in the form of a disposable, open-form diaper 100, as it might appear in a relaxed condition at rest on a table, prior to donning on an infant. FIGS. 2 and 3 depict plan views of the wearer-facing surfaces 11 and outward-facing surfaces 12, respectively, of the diaper of FIG. 1, laid out flat and extended to the full dimensions of its non-elastic components. A typical disposable diaper includes a chassis 100a with a front waist region 101, rear waist region 102 and crotch region 103, longitudinal axis 104 equally dividing the width of the chassis, and lateral axis 105 equally dividing the length of the chassis, longitudinal edges 106, front waist edge 107 and rear waist edge 108. The front waist region lies entirely to the front of the lateral axis 105; the rear waist region lies entirely to the rear of the lateral axis 105, and the crotch region longitudinally straddles the lateral axis 105.

Chassis 100a may be formed of a liquid-permeable topsheet 111 which forms a large portion of the wearer-facing surfaces; a liquid-impermeable backsheet 112 which forms a large portion of the outward-facing surfaces, and an absorbent core structure (not shown) disposed between the topsheet and a backsheet, within an enveloping structure formed by the assembly of topsheet and backsheet. The article 10 may also include a pair of elasticized outer leg cuffs 106, and a pair of elasticized inner barrier cuffs 115, which together serve dual purposes of providing for containment of wearer exudates and providing a neat, fitted appearance about the wearer's legs. These cuff structures may be formed separately or as an integral structure and assembled to overlay the wearer-facing side of the chassis 100a. The article may also include an elasticized waistband in the front waist region and/or an elasticized waistband in the rear waist region.

Diaper 100 also may include one or more fastening members 120, such as a pair of left and right fastening members 120 each affixed to and respectively extending laterally away from the longitudinal axis and the respective left and right longitudinal edges 106 of the chassis. Diaper 100 also may include a landing zone 130 on the front waist region. Fastening members 120 and landing zone 130 may include respective cooperating fastening components that enable fastening of fastening members 120 at locations proximate their laterally distal ends, to the landing zone 130. Thus, diaper 100 may be donned on an infant wearer with the rear waist region 102 covering the wearer's buttocks, the crotch region 103 wrapping under the wearer's lower torso between the legs, and the front waist region covering the wearer's lower front torso; and the fastening member 120 may be wrapped about a hip and then fastened at the landing zone 130, thereby fastening the diaper about and on the wearer. In some examples, fastening members 120 may be formed of, or include sections of, a stretch laminate material that imparts elastic stretchability and contractibility to the fastening members 120 along the lateral direction, enhancing the fit and comfort of the diaper for the wearer.

Non-limiting examples of suitable diaper and fastening member configurations are described and depicted in, for example, US 2018/0200125, and references cited therein.

Hooks Configurations; Hooks Formation

In many current examples of disposable diapers, fastening members 120 include patches of hooks adhered to wearer-facing surfaces of the fastening members 120, proximate their laterally distal ends. Correspondingly, in such examples the landing zone 130 will include a material adapted to fastenably cooperate with the hooks, such as section or patch of material adapted to serve as cooperative loops material, to provide a hook-and-loop fastening system combination. In some embodiments, the landing zone comprises a discrete material (e.g., a discrete path of loops material) that may be attached to the backsheet or other portion of the diaper. In some embodiments, the landing zone 130 may be integral with one or more portions of the diaper (e.g., loops material formed from or otherwise integral with said portions), such as one or more portions of the backsheet 112.

Figure 4:
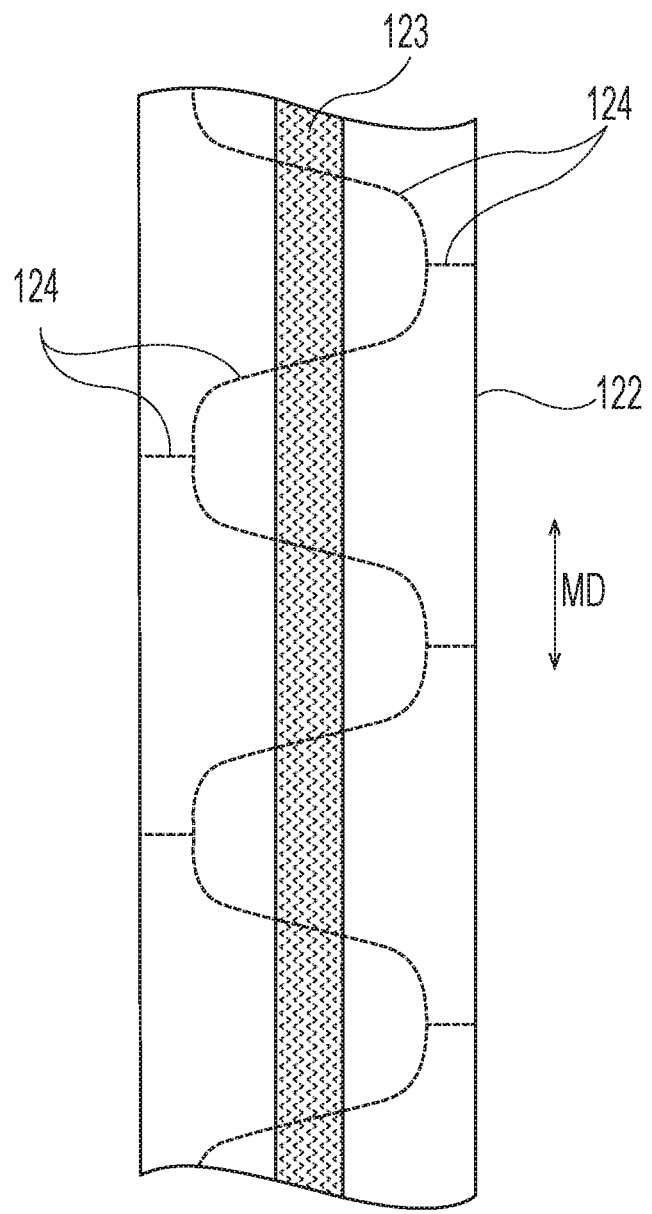
FIG. 4 is a plan view of a section of web material to which a strip of hooks material has been applied.
Figure 5:
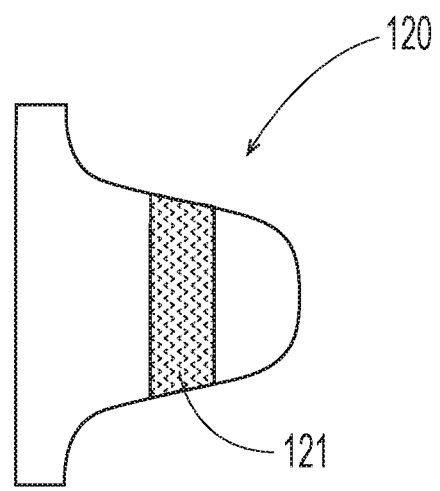
FIG. 5 is a plan view of an example of a fastening member cut from the web material shown in FIG. 4.

Referring to FIGS. 4 and 5, frequently, fastening members 120 with hooks patches 121 have been manufactured by providing a continuous web of fastening member substrate material 122, conveying it along a machine direction MD, unrolling hooks material strip from a rolled supply thereof and continuously adhering or bonding the strip 123 to the substrate material 122, and then cutting the substrate material with the adhered hooks strip along fastening member cut paths 124 that trace the profile desired for the fastening members 120, generally along directions transverse to the direction the hooks strip 123 was unrolled. As suggested in FIG. 4, for manufacturing efficiency and minimization of cut-off waste, the fastening member profiles and associated cut paths 124 may be nested along the substrate material. In the resulting cut-out fastening member 120 as reflected in FIG. 5, the hooks patch 121 is coextensive with the fastening member along the direction in which the hooks material strip was unrolled. It will be appreciated that this process involves the necessity of procuring a supply of hooks strip material 123, and providing equipment and process steps to unroll and adhere or bond the hooks material strip to the fastening member substrate 122. It will be appreciated further that this process creates constraints with respect to the size, shape and placement of the hooks patch relative the fastening member, including, among other constraints, that the resulting hooks patch 121 will be coextensive in machine direction length and shape with the cut lines 124.

More recently, integrally molding hooks directly on a substrate material has been proposed, wherein the substrate material serves not only as a structural component material for other purposes, but also as the source of polymer material for formation of the hooks; see, e.g., U.S. Pat. Nos. 8,784,722; 6,478,784 and 6,746,434. Products of these processes or similar processes are currently marketed by Soni-Form, LLC and/or Creative Machine Designs, Inc., both of Derry, N.H. These methods involve conveying a suitable substrate along a machine direction to a molding roll having hook-forming cavities formed in and along a circumferential molding surface thereof, combined with an opposing roller or other body providing an opposing surface, and a source of heating energy (for example, ultrasonic vibratory energy), to heat and soften a portion of the polymeric material of the substrate and press it into the hook-forming cavities. As the substrate leaves the molding roll/opposing surface combination, it has an array of hooks formed directly thereon, integral with the material of the substrate. It may be appreciated that when used with a suitable substrate, this process might be used to eliminate the need for process steps and materials associated with obtaining and supplying a strip of hooks material and applying and adhering or bonding it to the substrate, in order to provide a substrate bearing hooks.

Figure 6A:
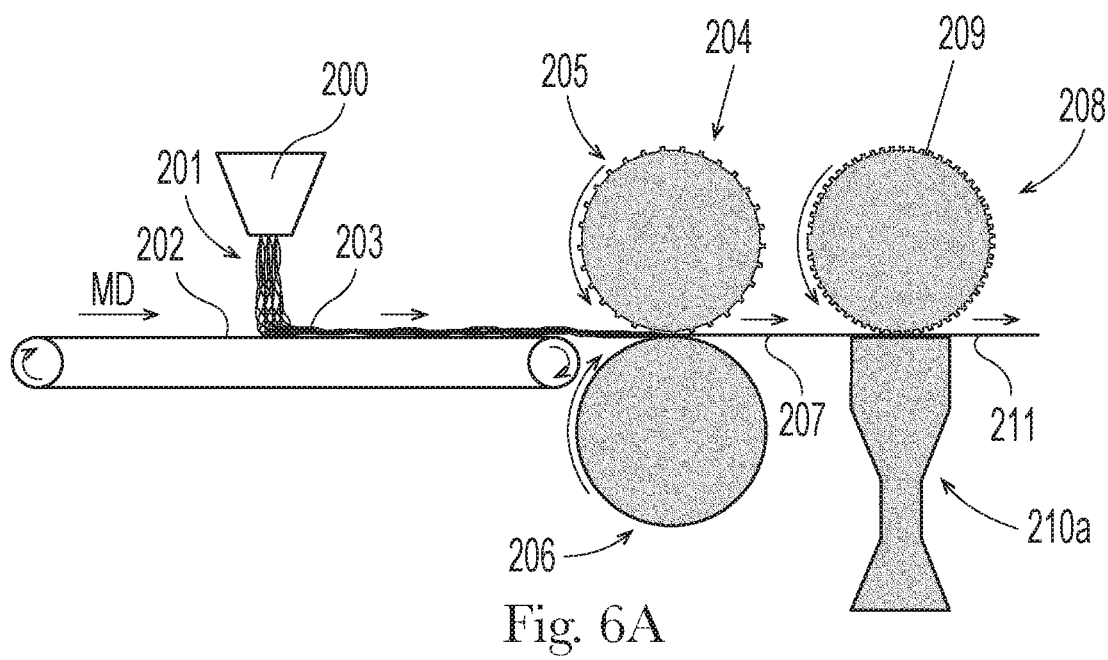
FIGS. 6A-6C are schematic side-view depictions of configurations of equipment and a schematic representation of examples of processes for manufacturing a bonded nonwoven web material with integrally molded arrays of hooks.
Figure 6B:
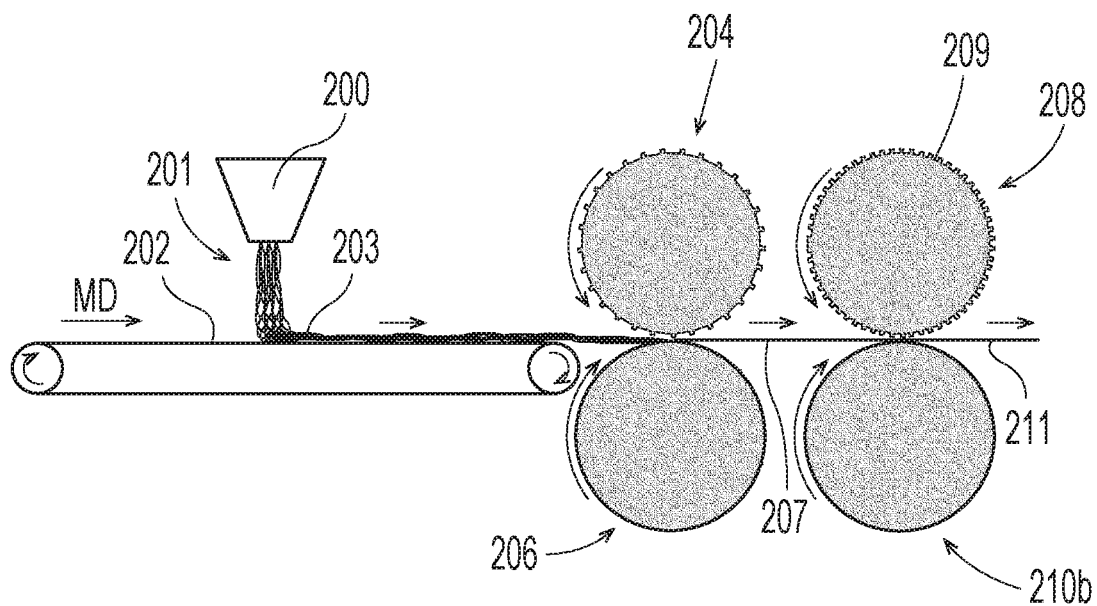
Figure 6C:
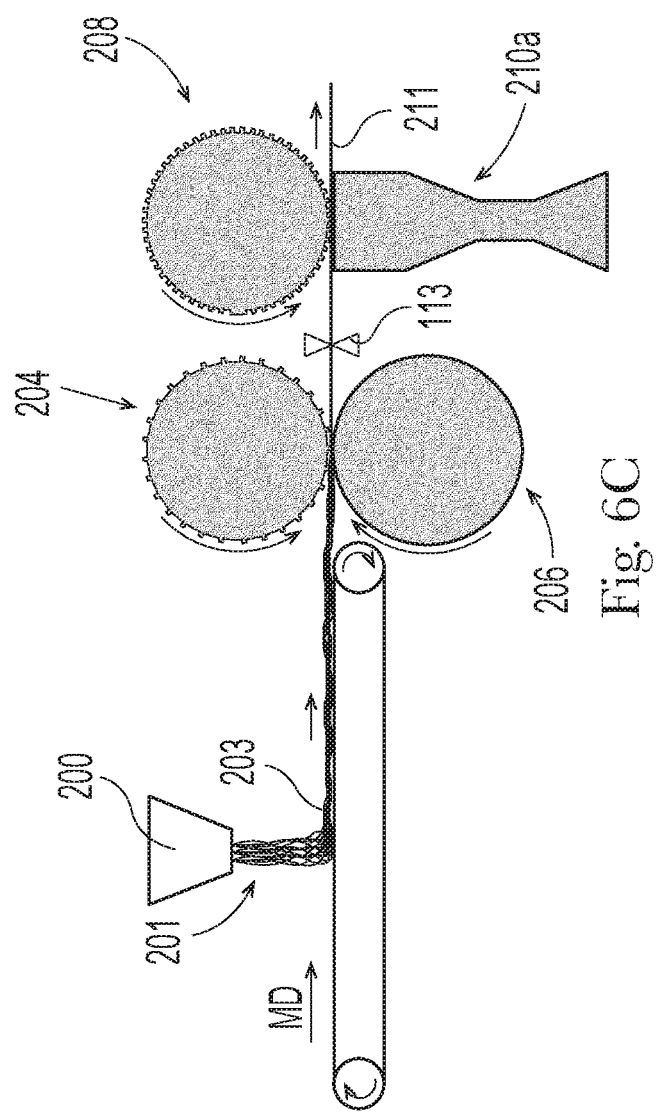

In a further application, the processes of forming nonwoven web material and forming hooks thereon might be combined in a single continuous process. Referring to FIGS. 6A and 6B, a bonded spunbond web may be formed by urging under pressure suitably selected polymeric material or materials in heated (molten) state through a beam of spinnerets 200 to spin filaments 201 and direct them to a conveyor surface 202 moving along a machine direction MD. As the spun filaments 201 strike the conveyor surface 202, they accumulate to form a batt 203 or deposition of unconsolidated filaments on the surface. Those of ordinary skill in the art of nonwoven web manufacturing appreciate that the basis weight of the batt 203 and of the finished web may be adjusted and controlled by controlling process variables such as, but limited to, the size of the beam of spinnerets 200 and numerical/spatial density of individual spinnerets therein; the rate at which polymer material is urged through the beam; and the speed at which the conveyor is operated. The filaments generally strike and come to rest within the batt on the conveyor surface in partially random but partially machine-direction biased directional orientations, as a result of machine direction movement of the conveyor surface as it receives the spun filaments.

The batt 203 may then be conveyed into the nip between a pair of calender/bonding rollers including a bonding roller 204 having bonding protrusions 205 arranged in a pattern and extending radially outwardly from the circumferential surface of the bonding roller, and an opposing anvil roller 206. A source of heating energy may be supplied proximate the nip. In some examples, one or both of the bonding roller 204 and anvil roller 206 may be heated. As the batt 203 moves into the nip, it is compressed along a z-direction and pressure on the batt is concentrated in the areas where the bonding protrusions approach the opposing surface of the anvil roller, resulting in at least partial melting and fusing of filaments beneath the bonding protrusions, and then resulting in a consolidated, bonded nonwoven web 207 with an impressed pattern of bonds that approximately correspond in size, shape and arrangement with the pattern of bonding protrusions on the bonding roller 204.

In some examples, the bonded nonwoven web 207 may be laminated with another similarly-formed nonwoven web, or a polymeric film, or both, to form a laminate web that includes two or more layers including the bonded nonwoven web 207.

Directly or indirectly downstream of the calender/bonding rollers, or laminating rollers, but disposed so as to perform steps in a continuous part of the same web processing operation, a hooks-forming roller 208 may be disposed. Hooks-forming roller 208 may have formed into its circumferential surface a pattern of hooks-forming cavities 209, configured to mold one or more continuous or discontinuous areas of hooks of desired shape, size, directional orientation, pattern, density and area shape and size. A source of heating energy such as, for example, ultrasonic vibratory energy (provided via, e.g., an ultrasonic horn or sonotrode 210a or a rotary ultrasonic horn 210b) may be disposed in opposition to the hooks-forming roller 208 to form a second nip. As the bonded nonwoven web 207 passes through the second nip, heating of the polymeric material of the filaments, by application of the heating energy, softens it so that it may be deformed and forced, in the second nip, into the hooks-forming cavities 209 of the hooks-forming roller. The hooks-forming roller 208 may be cooled or otherwise temperature-controlled to help assure that the finished web 211 will emerge from the second nip with formations of hooks that are stably formed and solidified. The resulting hooks and areas thereof on the emerged finished web 211 will be molded from and thereby physically integral with material(s) of which the nonwoven web material and/or laminate web is formed. Similar to the manner in which the pattern of bonds in the material correspond with the pattern of bonding protrusions on the bonding roller 204, the pattern of and shape of hooks that result on the finished web 211 will approximately correspond with the arrangement and features of the hooks-forming cavities 209 in the hooks-forming roller 208.

In another example, bonding protrusions and hooks-forming cavities might both be formed on a single combination bonding/hooks-forming roller. One or more of an anvil roller, heated anvil roller and a rotary ultrasonic horn may be disposed in opposition to the bonding/hooks-forming roller to form a nip therewith. A bonded nonwoven web bearing one or more areas of integrally molded hooks may be formed in single step by passing the batt of spun filaments through this nip.

Figure 7A:
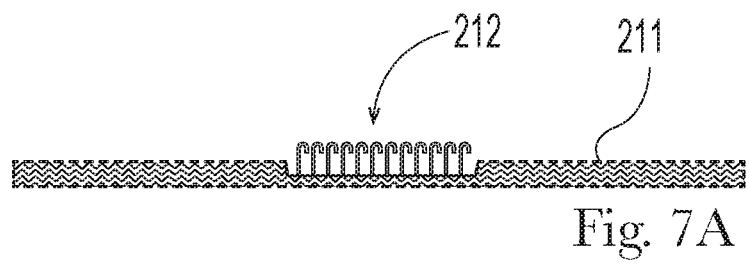
FIGS. 7A-7E are schematic cross-section views taken along a cross direction through exemplary web materials on which areas of hooks have been integrally molded.
Figure 7B:
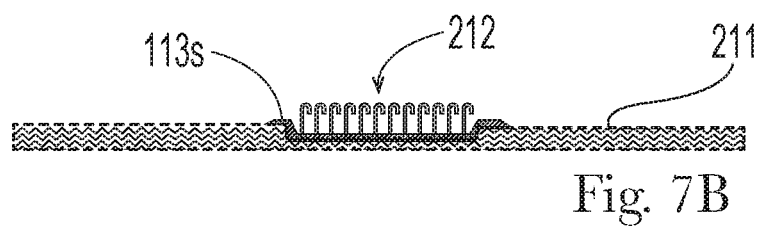
Figure 7C:
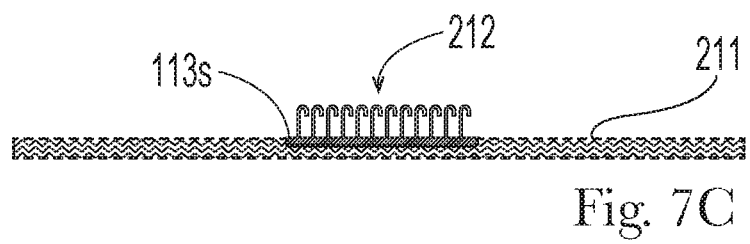
Figure 7D:
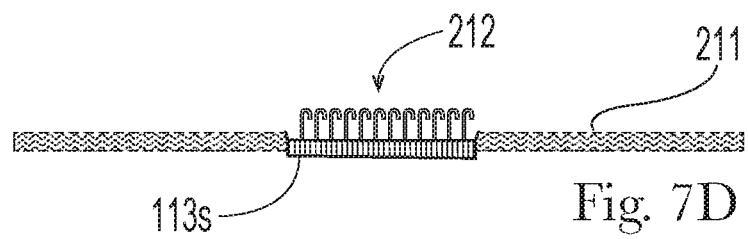
Figure 7E:
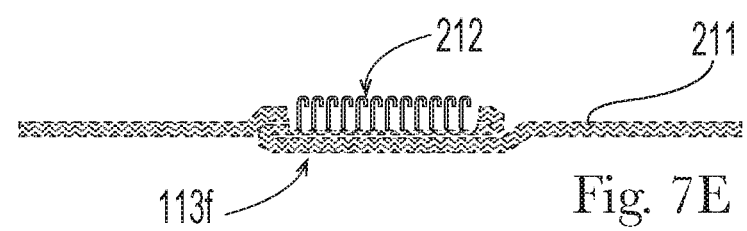

Referring to FIGS. 6C and 7B-7E, in some examples, it may be desired to provide supplemental thermoplastic polymer material 113s for molding hooks and forming a base structure therefor, over the web material 211, as suggested in FIGS. 7B and 7C, beneath the web material as suggested in FIG. 7D, or in some examples, by folding the web material 211 over on itself, as suggested in FIG. 7E (illustrating a non-limiting example of a Z-fold 113f of web material 211 with fold lines along the machine direction). In some examples, a supplemental thermoplastic polymeric material may be introduced upstream of the nip between the hooks-forming roller to provide the supplemental material 113s for forming integrally molded hooks. Referring to the example of a processing system illustrated in FIG. 6C, a selected quantity of supplemental material may be introduced to the web by a supplemental material delivery system 113, in a position along the web where it, in combination with the polymeric material forming the filaments, will be subject to the heating energy (e.g., ultrasonic vibratory energy) and be in suitable position to be at least partially urged into the hooks-forming cavities in hooks-forming roll 208. It may be desired that the supplemental polymeric material have substantially the same composition as the polymeric material from which the filaments are spun, or is otherwise of like chemistry therewith, to ensure that the polymeric material from which the filaments are spun and the supplemental polymeric material become suitably blended/merged and integral during and following formation of hooks and cooling. The supplemental polymeric material may have the form of a strip of film or nonwoven web material introduced along the machine direction, in line with the hooks-forming cavities, a deposition of molten polymeric material applied to the web either continuously or intermittently, etc.

Figure 8A:
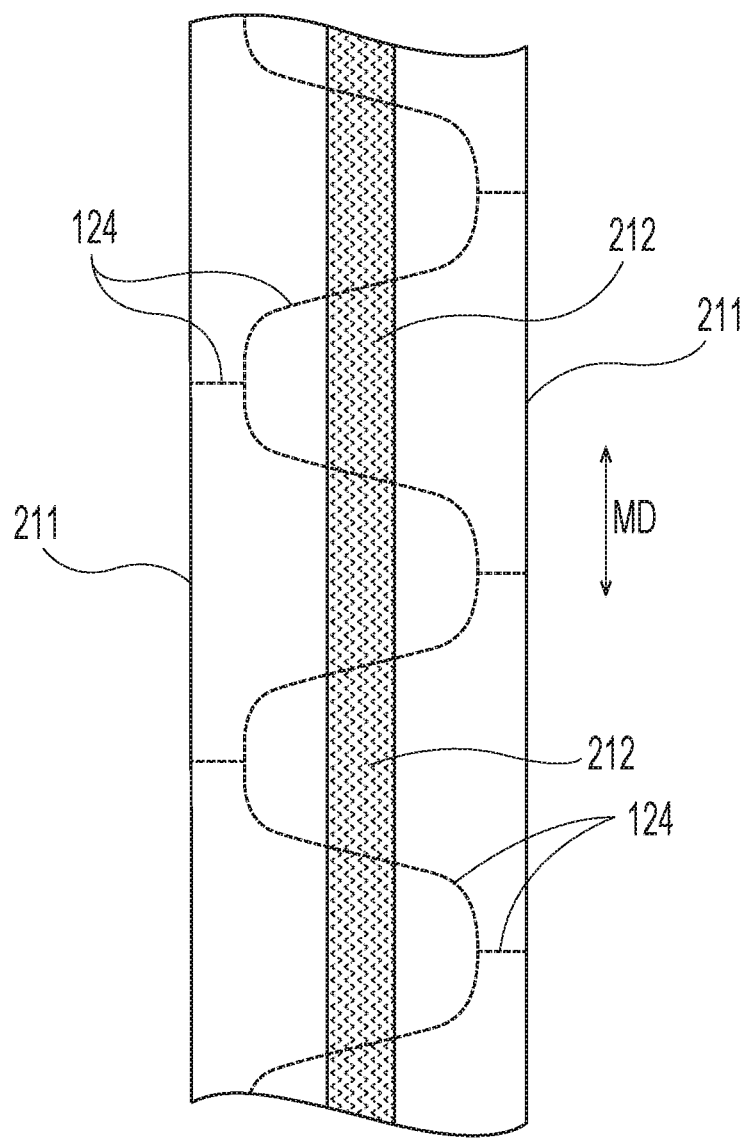
FIG. 8A is a plan view of a section of web material upon which a strip of hooks has been integrally molded.
Figure 8B:
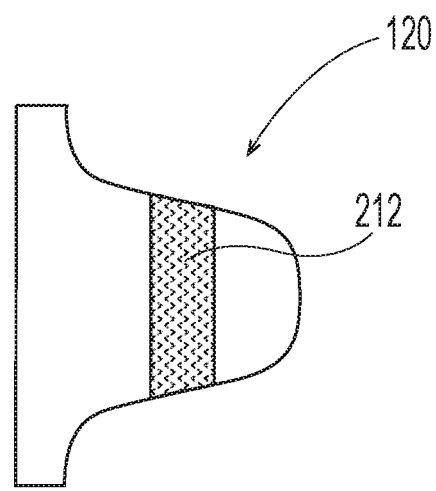
FIG. 8B is a plan view of an example of a fastening member cut from the web material shown in FIG. 8A.
Figure 8C:
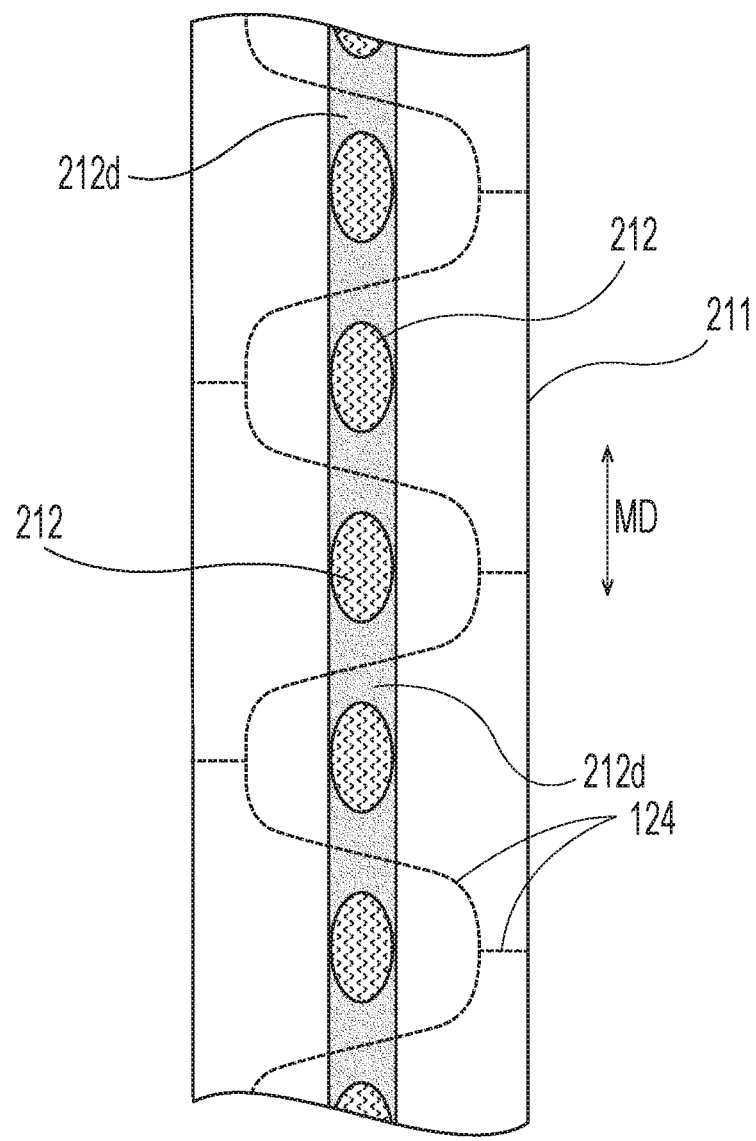
FIG. 8C is a plan view of another example of a section of web material upon which a strip of hooks has been integrally molded, having areas that have been subsequently deactivated or flattened.
Figure 8D:
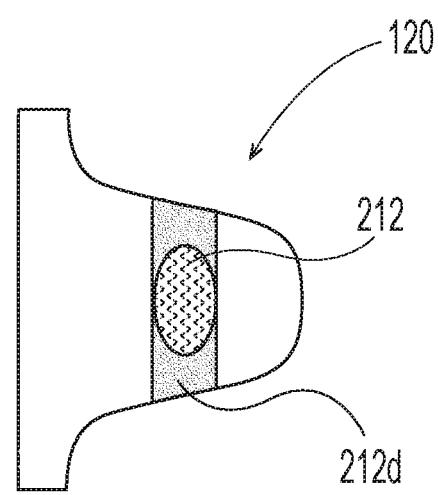
FIG. 8D is a plan view of an example of a fastening member cut from the web material shown in FIG. 8C.

Now referring to FIGS. 8A and 8C, in some examples, using suitably configured equipment, a continuous strip of hooks area 212, the strip being aligned with the machine direction, may be integrally molded on the substrate web material 211, such that integrally molded hooks extend to and through the upstream and downstream cut paths 124 and resulting cut edges of fastening members in the manner suggested in FIGS. 8B and 8D. In some more particular examples, such integrally molded hooks proximate the cut paths 124 or cut edges of the fastening members may be flattened in areas 212d by subsequent rolling or other suitable technique, to blunt or flatten the hooks and/or smooth the fastening members along their cut edges. This may be desired for aesthetic purposes, or to blunt/flatten hooks integrally molded on the fastening members in positions along the cut edges, decrease risk of wearer skin abrasion and/or irritation therefrom.

Figure 8E:
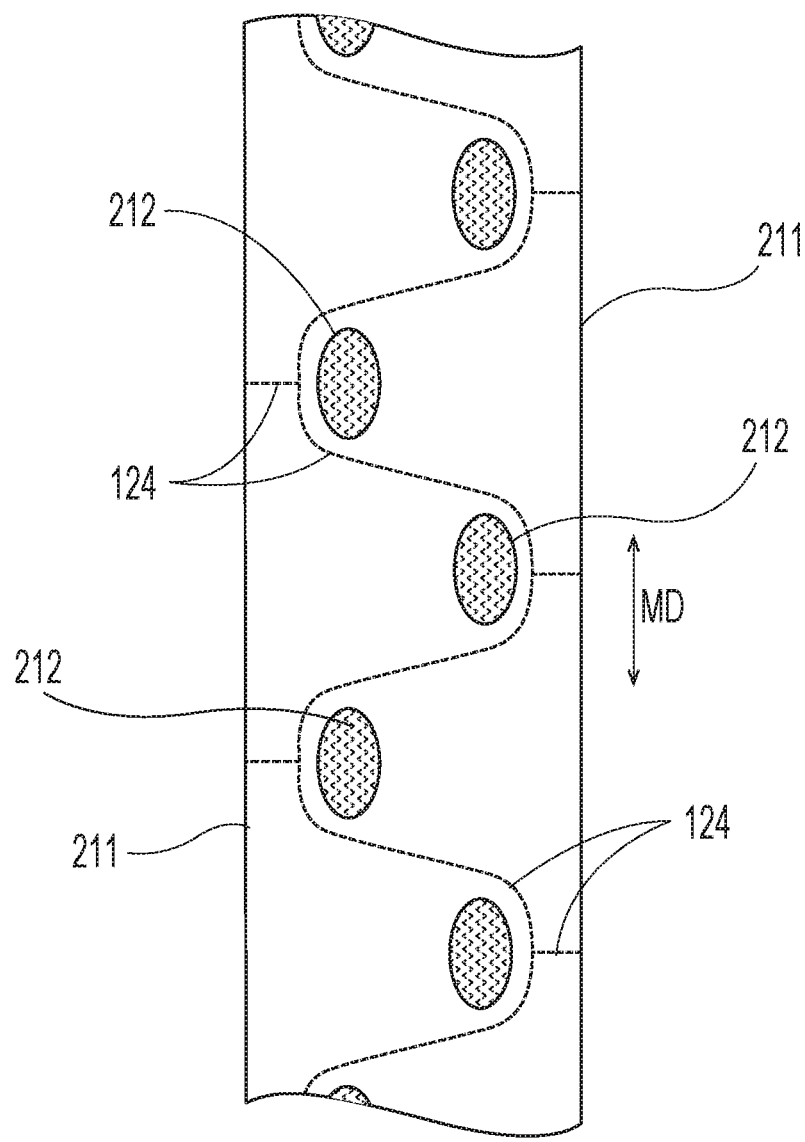
FIG. 8E is a plan view of another example of a section of web material upon which discrete areas of hooks have been integrally molded.
Figure 8F:
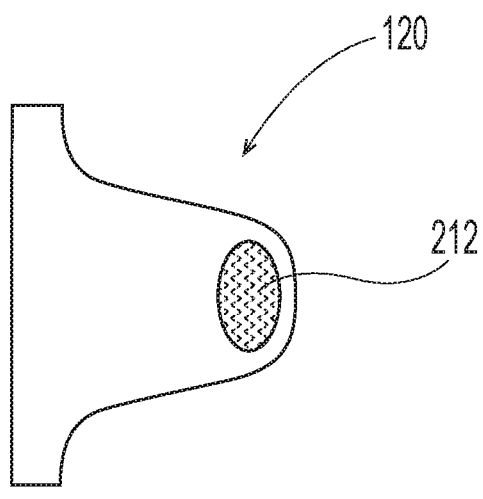
FIG. 8F is a plan view of an example of a fastening member cut from the web material shown in FIG. 8E.

Using a process as described above, however, and referring to FIGS. 8E and 8F, a finished web material 211 with integrally molded, discrete and separate areas of hooks 212 may be formed. Hooks-forming cavities may be formed and arranged on a hooks-forming roller in any desired configuration of hook size, shape, number, density, placement pattern, and arrangement of areas of hooks.

Using the online hooks molding process described, the practical constraints and/or costs presented by supply and application of a continuous strip of pre-manufactured hooks material are eliminated, and the areas of hooks may be provided on the nonwoven material in any desired configuration, such as the configurations reflected in FIGS. 8A-8G. Additional illustrative but non-limiting examples of hooks area configurations are depicted in FIGS. 9A-9E. It can be appreciated that areas of hooks may be configured in any desired size, shape, pattern, directionality of hooks orientation, number of hooks, etc. Areas of hooks may be configured as discrete, discontinuous shapes entirely surrounded by areas not occupied by hooks, as may be seen in FIGS. 9B, 9D and 9E (sometimes known as "islands-in-the-sea" configurations). Continuous areas of hooks may be configured to entirely surround discrete, discontinuous shapes of areas not occupied by hooks, as may be seen in FIG. 9A. Any combination of these two features is also contemplated, for example, the configuration shown in FIG. 9C.

Features of an "integrally-formed" fastening member are disclosed in US 2014/0200543, U.S. Pat. Nos. 9,333,125 and 9,068,912. Referring to FIG. 9 of the '125 patent, for example, such features may include first and second surface layers (62 and 63, in FIG. 9 of the '125 patent) that extend continuously from a proximal portion of the fastening member to a distal end. As described in the '125 patent, a fastener such as a patch of hooks may be affixed to one of the surface layers at a location proximate the distal end. The fastening member may be elasticized to have elastic stretch capability as described in the '125 patent, including by way of inclusion of an elastomeric material layer (64, in the '125 patent) disposed between the surface layers, in a laminate. The described fastening member construction provides an integrated structure for a fastening member, that may be efficiently manufactured and eliminates any need for a separate tape tab with hooks to be affixed to a distal end of the member.

Features and construction of the fastening members described in the '125 patent and/or '912 patent and/or '543 application may be combined with integrally-molded hooks as described herein, whereby integrally molded hooks are formed on the fastening members in substitution for the separate patches of hooks material described in the references. Additionally, or alternatively, integrally molded hooks may be formed in the front waist region, on the landing zone or elsewhere in the front waist region, in lieu of the patches of hooks material described in the references.

Figure 8G:
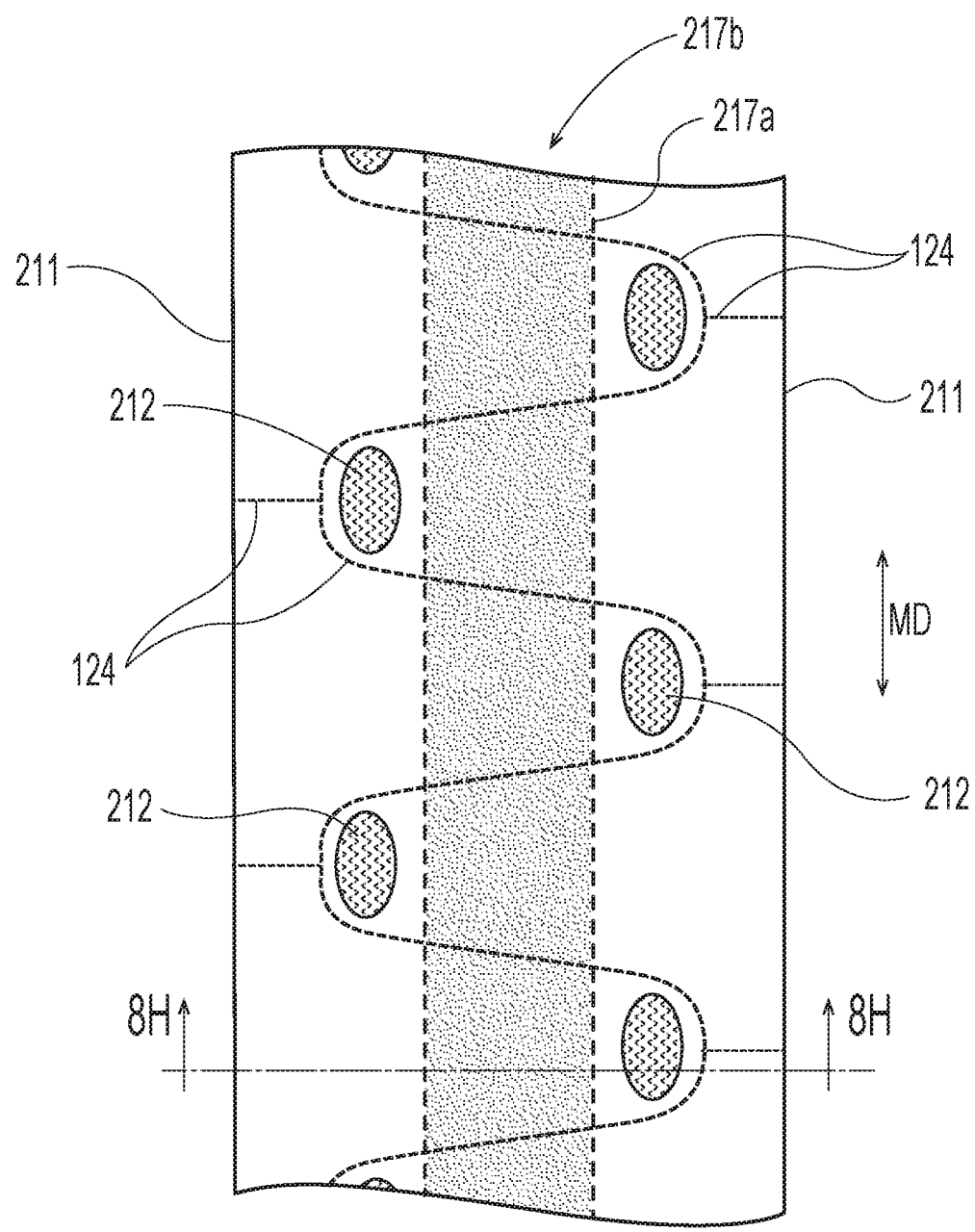
FIG. 8G is a plan view of a section of web material upon which discrete areas of hooks have been integrally molded, wherein the web material includes an elasticized zone.
Figure 9A:
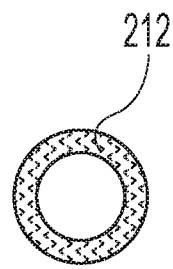
FIGS. 9A-9E are depictions of various examples of arrangements of areas of hooks.
Figure 9B:
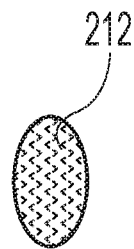
Figure 9C:
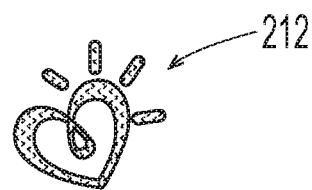
Figure 9D:
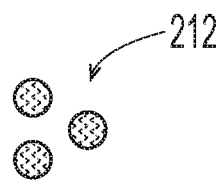
Figure 9E:
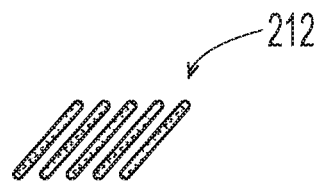
Figure 10A:
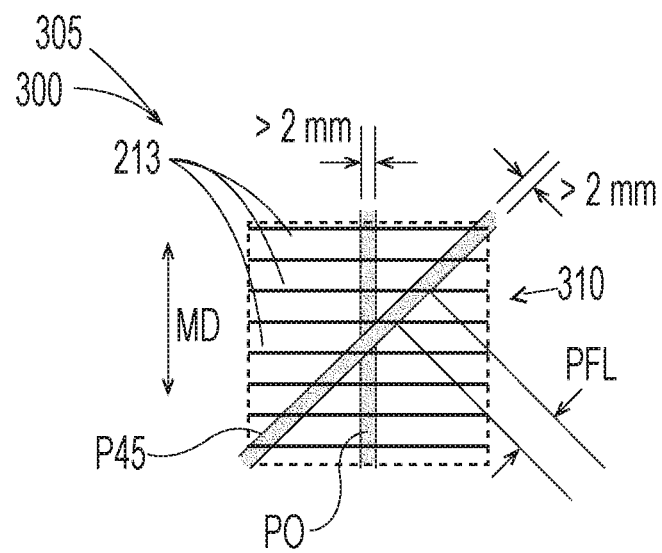
FIGS. 10A-10I and 11A-11C are depictions of various examples of bonding patterns on sections of nonwoven loops material.
Figure 10B:
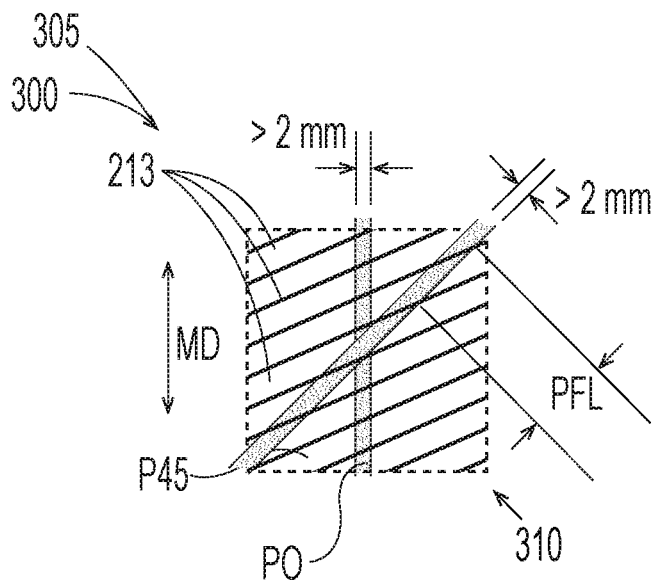
Figure 10C:
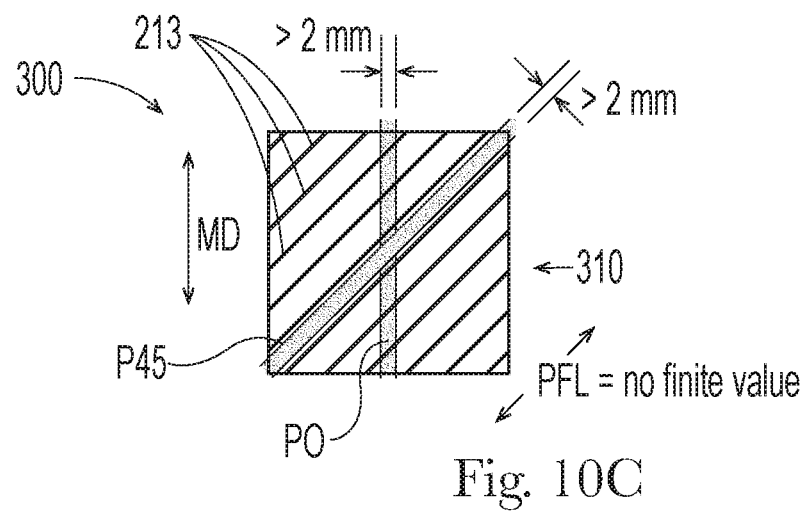
Figure 10D:
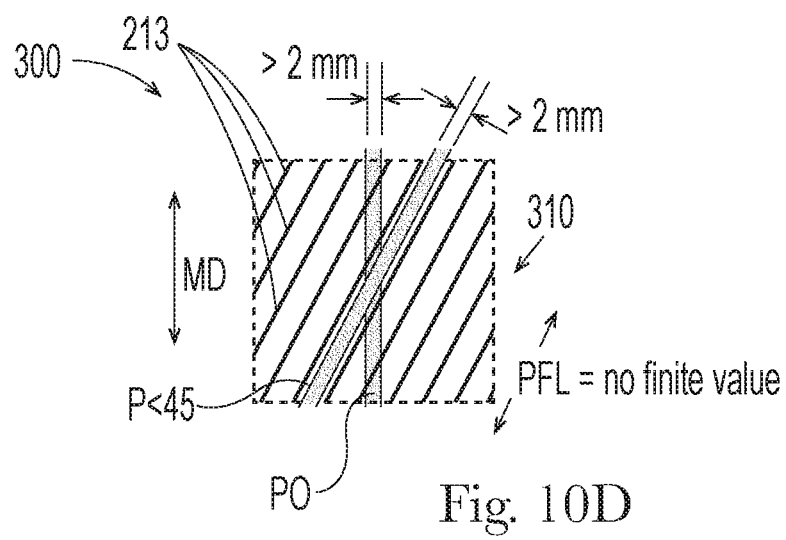
Figure 10E:
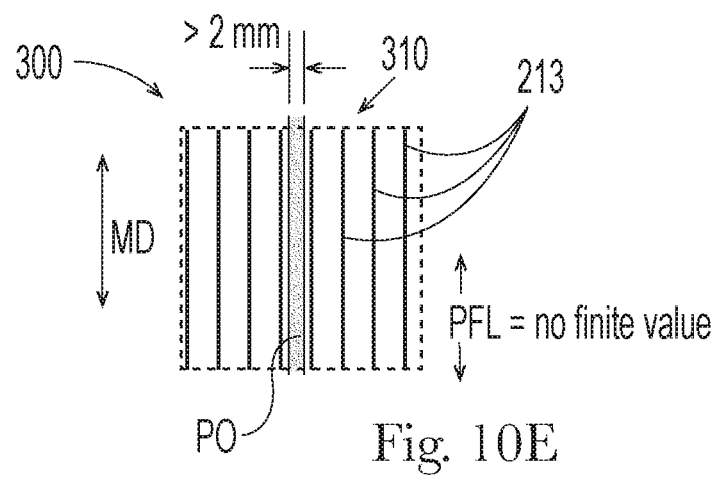
Figure 10F:
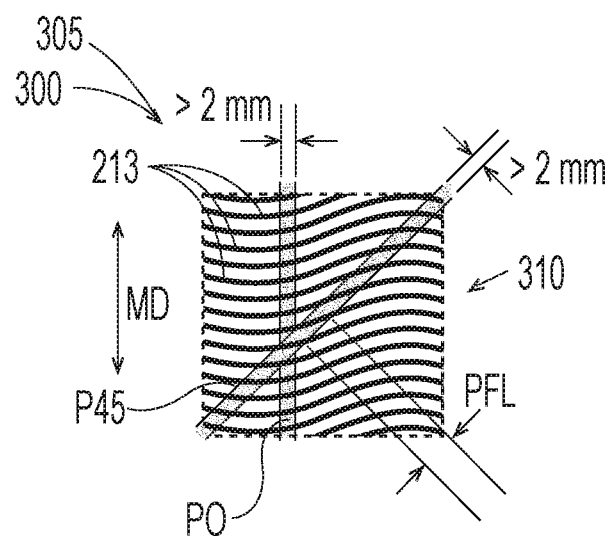
Figure 10G:
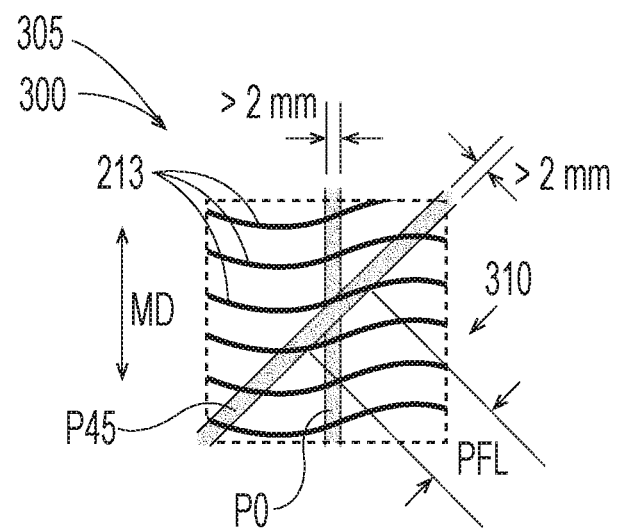
Figure 10H:
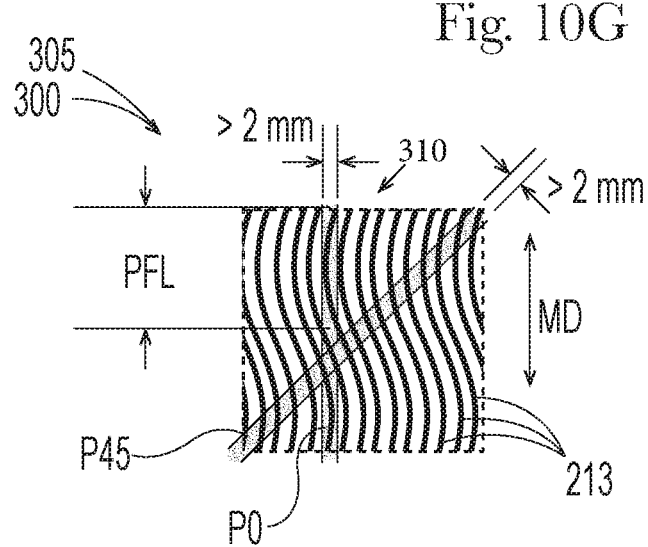
Figure 10I:
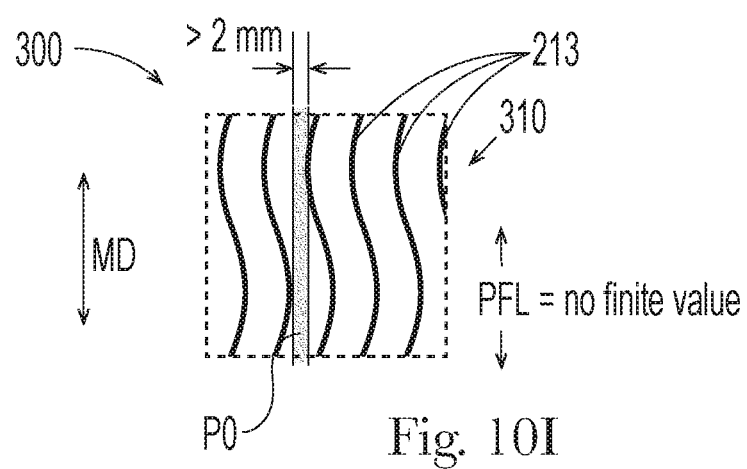
Figure 11A:
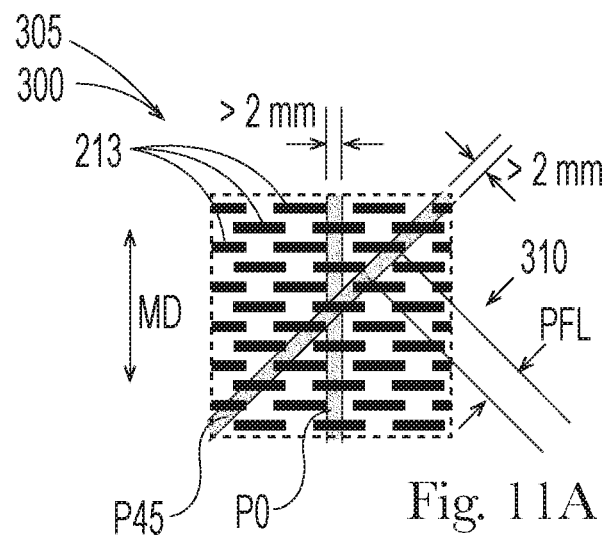
Figure 11B:
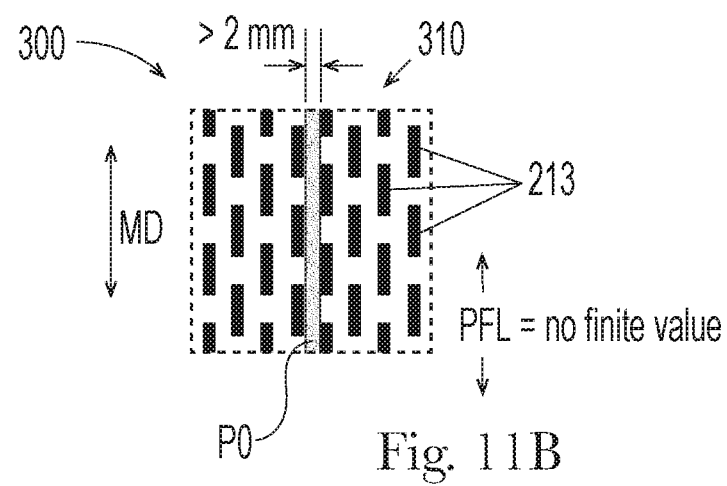
Figure 11C:
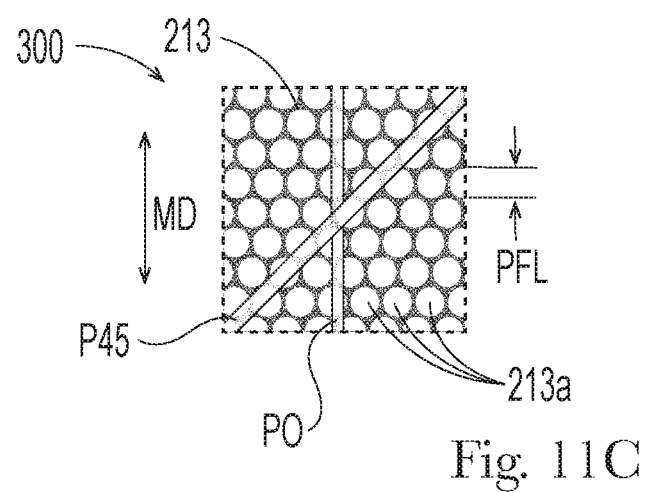

Referring to FIGS. 8G and 8H, for example, a laminate web 211 may be formed of first layer 211a and second layer 211b. Layers 211a, 211b may sandwich and be laminated about an elastic material 217a, which may in some non-limiting examples an elastomeric film, to form an elasticized zone 217b of the laminate web 211. The layers may be affixed together to form a laminate via any suitable means, including for example adhesive bonding and/or mechanical bonding between the layers. The laminate 211 may comprise a gathered laminate, wherein one of the layers is strained to a greater degree than a remaining layer during lamination. In this way, the less extensible layer (i.e., a nonwoven) will form gathers when the laminate is in a relaxed state. Corrugations then form in the nonwoven layer(s) when the subsequently formed laminate is in a relaxed state. The laminate may comprise an ultrasonically bonded laminate as is disclosed for example in U.S. Pat. Pub. Nos. 2018/0042777, 2018/0042778; 2018/0271716; and 2018/0271717. Alternatively, the laminate 211 may be incrementally stretched, or may be activated by processes disclosed in U.S. Pat. Pub. No. 2013/0082418, U.S. Pat. Nos. 4,834,741; 5,167,897; 5,993,432; 5,156,793; 5,167,897; 7,062,983 and 6,843,134 for example. The web may be incrementally stretched or activated in the cross direction through the elasticized zone 217b, as is known in the art, to impart the web 211 and thereby fastening members to be cut therefrom, with elastic stretch and contraction capability along the cross direction, in the elasticized zone. As part of the manufacturing process, areas of integrally molded hooks 212 may be formed as described herein on portions of the web proximate to distal ends of fastening members to be cut from the web, as demarked by fastening member cut paths 124. Combining integrally molded hooks with other features of fastening members described in the '125 and '912 patents provides for an even more integrated and efficiently manufactured fastening member than that described in the referenced patents.

As indicated, the fastening member 120 may be formed discretely from the chassis. This may permit separate orientation of the fastening member and the chassis, or chassis components, during manufacturing, providing a greater degree of freedom in equipment set up, process steps and/or final diaper design.

Loops Material; Combination with Integrally Molded Hooks

In some examples, a nonwoven material may be manufactured using the method described above, such that the material possesses structure making it suitable for serving as both loops material and as hooks material. In nonlimiting examples, such nonwoven material may serve as the backsheet or a portion of the backsheet of the article 10. Spunbond nonwoven material may be manufactured for use in its entirety, or in one or more discrete sections, as loops material to be used as the loops fastening component of a hook-and-loop fastening system.

In some examples, the nonwoven material may be formed primarily or entirely of single-component spun filaments. In other examples, the manufacturing equipment and materials selections may be configured and adapted to spin bi-component or multi-component filaments, having differing, discrete portions of differing polymer composition extending along their spun lengths. As a result of differential rates and extents of contraction of these differing portions upon cooling, bi-component or multi-component filaments may tend to curl or crimp following spinning, making them particularly suitable for making loops material.

Returning to FIGS. 6A-6C, in some examples, filaments 201 are spun and directed to and deposited on a conveyor surface 202 to form a batt 203, as described above, under process conditions that impart a machine direction bias to the filaments. The batt may then be passed into the nip between a pair of calender/bonding rollers as described above, resulting in a bonded nonwoven web in which the filaments have a machine direction bias. To make the resulting bonded nonwoven web material, or sections thereof, suitable for use as loops material, the pattern of bonding protrusions 205 on the bonding roller 204 may be configured with features that ensure that most or all of the filaments of the intended section of loops material 300 are bonded in a suitable bonding pattern 310, such that they serve as effective, relatively closely-bound loops structures. Thus, when the filaments have a machine direction bias, it may be advantageous that the pattern of bonds have certain geometric characteristics, for at least the section(s) of the web to intended to serve as loops material 300.

Herein, a "section of loops material" 305 is any continuous section or continuous portion of nonwoven web material formed of spun filaments having a machine direction bias, the section or portion having a machine direction dimension of at least 20 mm, a cross direction dimension of at least 20 mm, and a surface area of at least 314 mm$^2$, which section or portion is calender bonded in a pattern of loops-forming bonds having geometric features as described below.

The geometric features may include conformity with geometric constraints on any paths of unbonded areas across the section or portion of material. FIGS. 10A-10I and 11A-11C schematically depict intended loops material 300 of the minimum machine- and cross-direction dimensions set forth above and bonded in various patterns 310. As will be further explained, the examples of patterns depicted meet, or do not meet, one or both of the constraints described below. The table below summarizes the extent to which these various examples meet the constraints described.

First Constraint: The section of intended loops material 300 may include one or more identifiable linear paths. By "identifiable linear path", it is meant that a path (a) has a width greater than 2 mm and (b) forms an angle of 45 degrees or less with the machine direction, in x-y plane along a major surface of the section of intended loops material. In the figures, examples of such identifiable linear paths are labeled "P0", "P45", and "P<45", where P0 is aligned with the machine direction (forms an angle therewith of 0 degrees); P45 forms an angle of 45 degrees with the machine direction; and P<45 forms an angle with the machine direction greater than 0 degrees and less than 45 degrees.

A first constraint that may be desirable is that every identifiable linear path along the section of intended loops material at least partially overlies a bond or bonds 213 in the pattern 310 at a plurality of locations along the path.

Second Constraint: The maximum identifiable dimension, PFL, between locations at which bonds are overlaid by any identifiable linear path is from 1 mm to 12 mm, more preferably from 2 mm to 10 mm, and even more preferably from 2 mm to 8 mm.

The following table summarizes the extent to which the examples of bond patterns depicted in FIGS. 10A-10I and 11A-11C meet the first and second constraints described above:

| FIG(S) | First Constraint | Second Constraint |
| --- | --- | --- |
| 10A, 10B | Met - every identifiable linear path greater than 2 mm wide, forming an angle of 45 degrees or less with machine direction MD (e.g., paths P0, P45), overlies bonds 213 at a plurality of locations | Met, if PFL is within one of the ranges specified in description above |
| 10C | Not met - identifiable path P45 does not overlie bonds 213 at any locations | Not met - PFL has no finite value |
| 10D | Not met - identifiable path P < 45 does not overlie bonds 213 at any locations | Not met - PFE has no finite value |
| 10E | Not met - identifiable path P0 does not overlie bonds 213 at any locations | Not met - PFL has no finite value |
| 10F, 10G, 10H | Met - every identifiable linear path greater than 2 mm wide, forming an angle of 45 degrees or less with machine direction MD (e.g., paths P0, P45), overlies bonds 213 at a plurality of locations | Met, if PFL is within one of the ranges specified in description above |
| 10I | Not met - identifiable path P0 does not overlie bonds 213 at any locations | Not met - PFL has no finite value |
| 11A | Met - every identifiable linear path greater than 2 mm wide, forming an angle of 45 degrees or less with machine direction MD (e.g., paths P0, P45), overlies bonds 213 at a plurality of locations | Met, if PFL is within one of the ranges specified in description above |
| 11B | Not met - identifiable path P0 does not overlie bonds 213 at any locations | Not met - PFL has no finite value |
| 11C | Met - every identifiable linear path greater than 2 mm wide, forming an angle of 45 degrees or less with machine direction MD (e.g., paths P0, P45), overlies continuous bond 213 (continuous region shown in black) at a plurality of locations (unbonded areas are discrete white circular areas 213a) | Met, if PFL is within one of the ranges specified in description above |

Configuring the bond pattern in observance of one or both the first and second geometric restrictions described above, minimizes the likelihood that substantial numbers of excessively long, unbonded lengths of filaments of the nonwoven web material, which are generally not suitable as loops structures, will be present. Conversely, observance of one or both of these restrictions provides that the substantially greater proportion of filaments making up the nonwoven web material will be bonded down to the web at intervals a suitable distance apart, making them suitable to perform as loops structures. With respect to the second constraint, a lower limit on the distance between bonds may be desired so that unbonded lengths of filaments are not too short to be accessible to hooks so as to be effectively engageable therewith; and an upper limit on the distance between bonds may be desired so that unbonded lengths of filaments are not too long to provide close engagement and holding strength when the section of loops material is engaged with hooks.

In conjunction with one or both of the geometric constraints described above, it may be desired to specify a range for the quantity of bonded surface area as a percentage of total surface area [typically expressed as "bond area percentage," or similar expression, calculated as (bonded area)/(total area)×100%]. If the bond area percentage is too low, there may be an insufficient amount of bonding to impart holding strength to the section of material. If the bond area percentage is too high, too many of the filaments and/or too much of their length will be rendered unavailable to engage hooks. Accordingly, it may be desired that the bond area percentage be controlled (via design of the bonding pattern) to be from 5 percent to 40 percent, more preferably from 8 percent to 25 percent, and even more preferably from 10 percent to 20 percent.

Alternatively, or in addition to the observance of the constraints described above, a section of intended loops material 300 may be bonded in a pattern according to any of the non-limiting examples described in U.S. Pat. No. 7,789,870.

To determine whether a bonding pattern conforms with the constraints and features described above, the pattern as visible on the nonwoven material may be viewed and measured by direct examination of the material (machine-assisted to any extent deemed helpful). It will be understood, however, that the geometric arrangement of a pattern of bonds impressed on a calender-bonded nonwoven web material will correspond approximately with the geometric arrangement of the pattern of bonding protrusions on the calender bonding roller used to bond the web. Accordingly, as an alternative to measuring the geometric arrangement of the bonding pattern by direct examination of the nonwoven web, the geometric arrangement of the bonding protrusions as formed on the calender roller may be examined and measured. In still another alternative, the geometric arrangement of the bonding protrusions as formed on the calender roller may be discerned from the specifications and/or mechanical drawings used to produce the calender roller. To the extent there may be some variance, between the geometric arrangement of the bonding protrusions on the calender roller as set forth in the specifications and/or mechanical drawings for the calender roller, the actual geometric arrangement of bonding protrusions on the calender roller, and the resulting actual geometric arrangement of the pattern of bonds impressed on calender-bonded nonwoven web material, the deviation is deemed to be within contemplation and scope of the numerical values for the constraints as described herein. Accordingly, if any of:

(a) the pattern of bonds actually present on the nonwoven web material, (b) the pattern of bonding protrusions actually present on the associated calender bonding roller, or (c) the pattern of bonding protrusions for the calender bonding roller as set forth in the specifications and/or mechanical drawings associated with the roller are in conformity with the geometric features and constraints described above, the pattern is deemed to be within contemplation and scope of the same.

A nonwoven material that is both adapted to serve as a loops material and has integrally molded areas of hooks formed therein, may be deemed useful for diapers with hook-and-loop fastening systems sometimes known as "multipoint" systems, or systems having "primary" and "secondary" pairs of hooks and loops, such as disclosed, in, for example, U.S. Pat. Nos. 9,265,673; 9,339,425; 9,597,237; US 2017/065,468; U.S. Pat. Nos. 9,615,980; and 9,265,674.

Examples of Configurations

FIGS. 12A-12E depict examples of sections of nonwoven web material 214 that might be included as, or as part of, a landing zone 130 on the front waist region of a diaper 101 (FIGS. 1 and 3). Section of nonwoven web material 214 may be bonded in a pattern of bonds that make it suitable for serving as loops material 300, for example a section of loops material 305 as described above. Additionally, section of nonwoven web material 214 may include areas of hooks 212 that are integrally molded on the material as described above. It will be appreciated that methods described herein may be used to form such sections and as such may be used to provide a nonwoven web material that includes both hooks and loops, without the need for process steps associated with supplying, applying and adhering or bonding previously manufactured hooks material, as a separate component, to the nonwoven web material. In nonlimiting examples, the section of nonwoven web material 214 may comprise a section of the article's backsheet 112. The section of nonwoven web material 214 may be discrete from the backsheet 112. By way of nonlimiting example, a section of nonwoven material 214 having hooks and loops material located in the rear waist region may be discrete from the backsheet, as shown for example in FIG. 13A. In further nonlimiting example, a section of nonwoven material 214 having hooks and loops material located in the front waist region may be integral with the backsheet.

The areas of hooks 212 may be configured so as to reduce the likelihood that hooks will contact the wearer's skin, along locations proximate the lower outside corners of the landing zone 130, should the diaper tend to bunch or fold at those locations, during wear. To provide such advantage, each area of hooks 212 may be configured that no hooks are present in the configuration within a 45-45-90 right triangle 217 with legs 5 mm in length, occupying the lower outside corner of a rectangle 215, with two sides parallel/along the lateral direction, drawn to entirely circumscribe the hooks area(s) present. It can be seen that the examples of hooks area 212 configurations in each of FIGS. 12A-12E all satisfy this condition. Accordingly, these nonlimiting examples would reduce the likelihood that hooks in the hooks areas 212 would contact the wearer's skin during wear of the diaper.

Figure 12A:
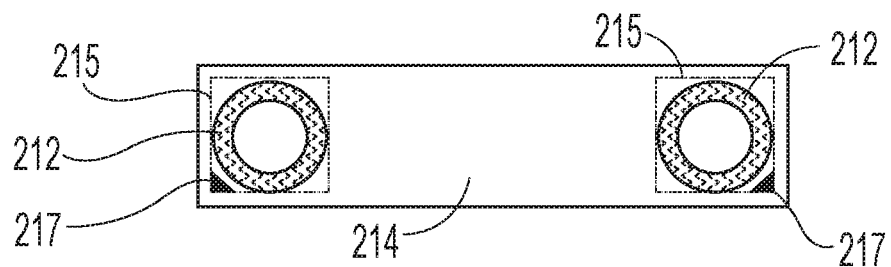
FIGS. 12A-12E are depictions of various examples of sections of web material upon which examples of hooks arrangements might be formed for use on a diaper.
Figure 12B:
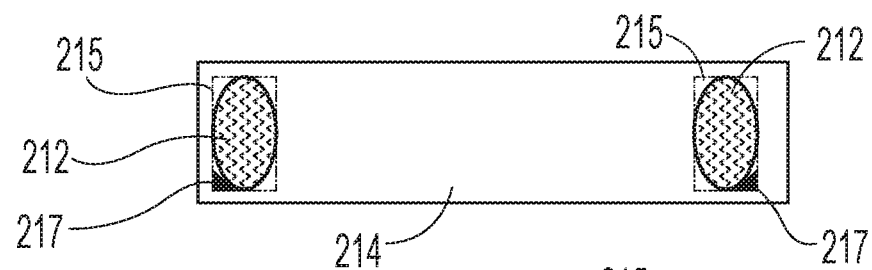
Figure 12C:
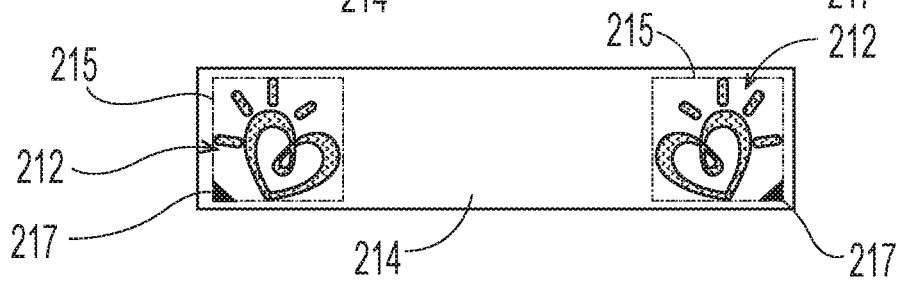
Figure 12D:
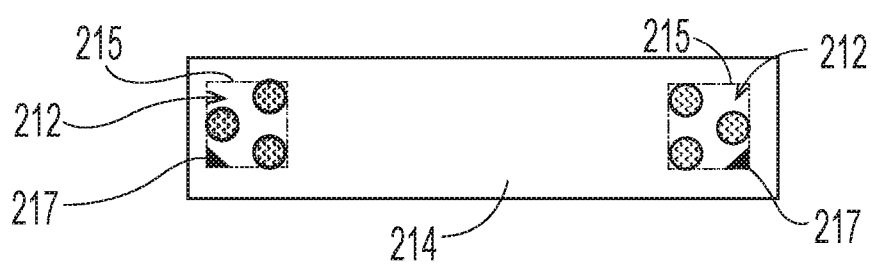
Figure 12E:
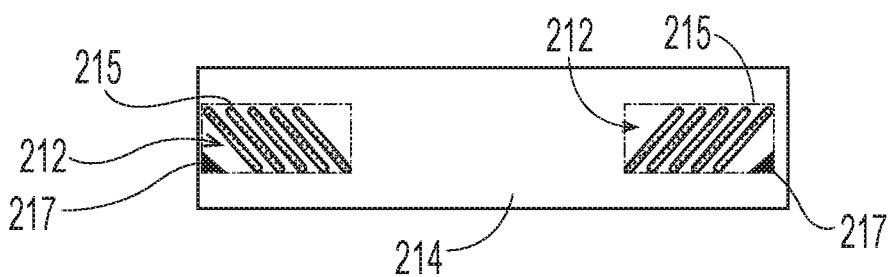
Figure 12F:
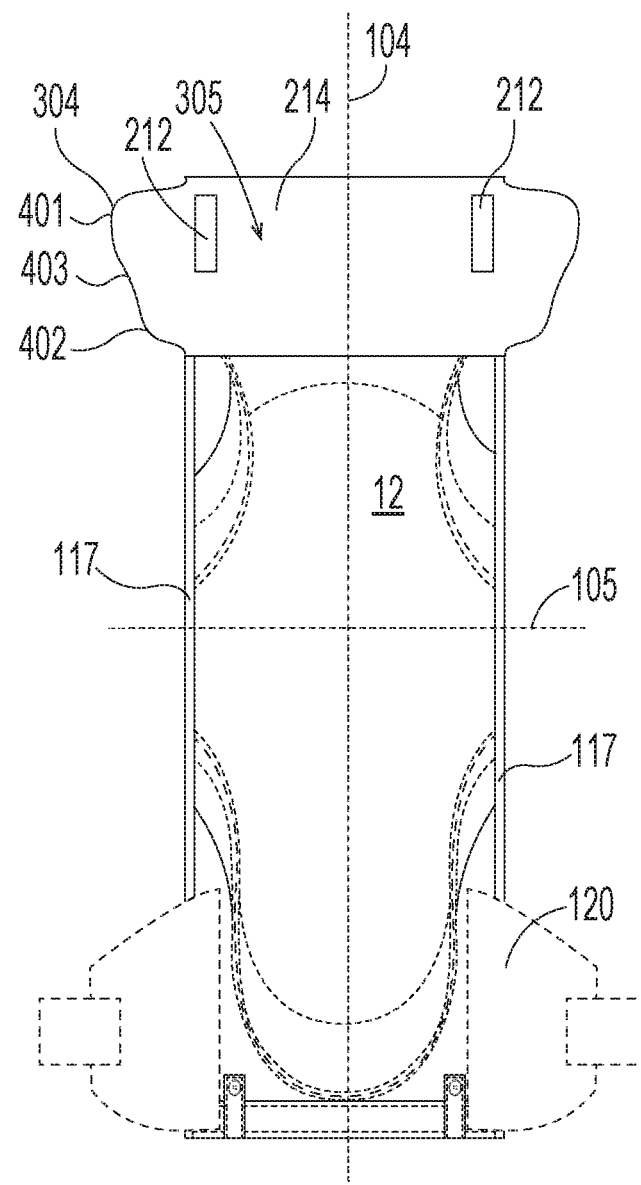
FIG. 12F is a plan view of a diaper, shown extended against contraction induced by elastomeric components, to substantially the full dimensions of its non-elastic components, shown with outward-facing surfaces facing the viewer.

As shown in FIG. 12F, when applied to the chassis, a longitudinal edge 304 of the web material 214 may extend outboard of the chassis longitudinal edge 117. Additionally, or alternatively, the section of web material 214 may comprise a curvilinear longitudinal edge 304. The curvilinear shape may have at least two convexities 401 and 402 and at least one concavity 403 disposed intermediate the two convexities. Without wishing to be bound by theory, it is believed this embodiment allows the belt to fit smoothly into the body's complex geometry and provides a more comfortable wearing experience by allowing the wearer's legs to move with less hindrance from material (i.e., the belt is narrower near the upper thighs) while maintaining a secure fit around the waist. In addition, minimizing the amount of material proximate to the inboard edge reduces the likelihood of the material folding over when positioned beneath under the back ear during application, and thereby increases fit and comfort.

Figure 13A:
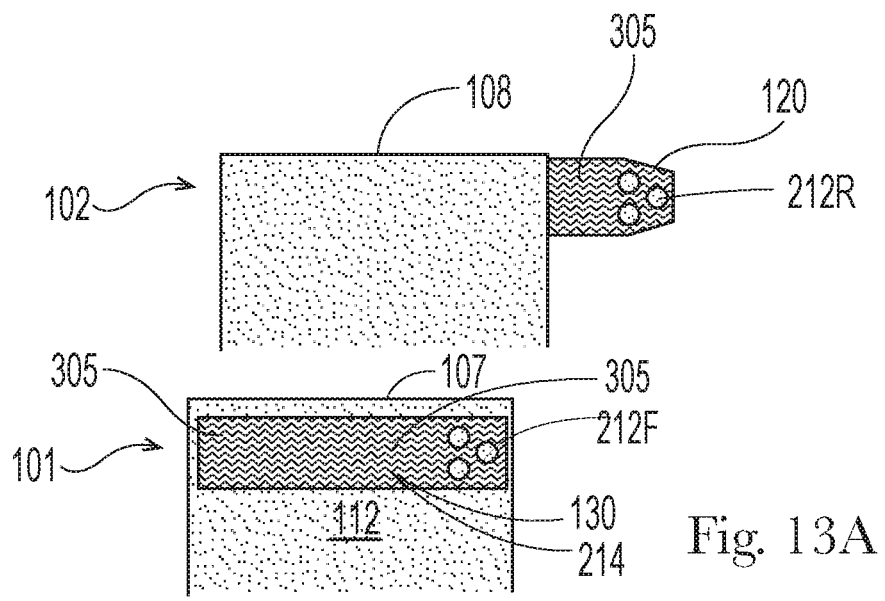
Figure 13B:
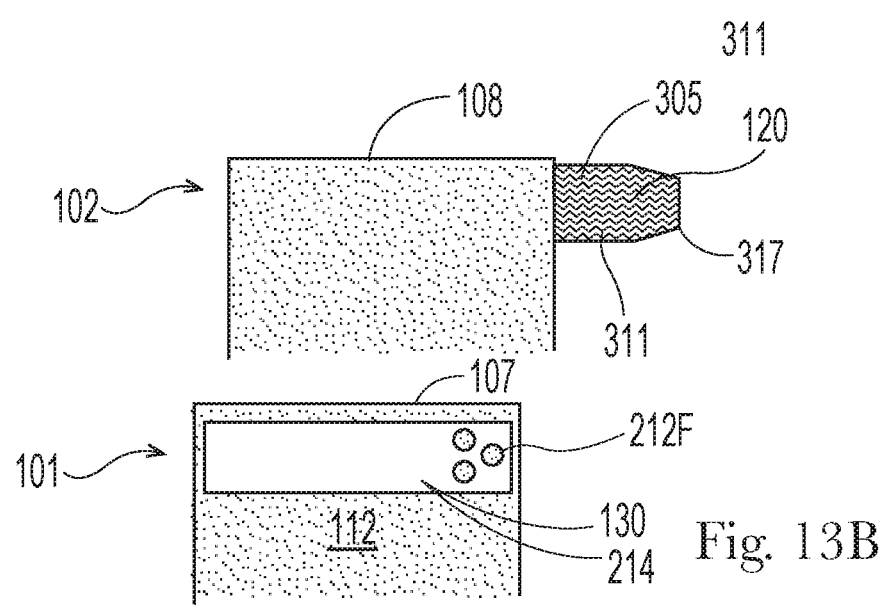

FIGS. 13A-13C depict non-limiting examples of configurations of features for diapers with hook-and-loop fastening systems that are contemplated herein. Referring to FIG. 13A, front waist region 101 may include a landing zone 130 formed by, or including, a section of web material 214 on which one or more areas of hooks 212F are integrally molded as described herein. Section of web material 214 may be adapted to serve as loops material 300, such as a section of loops material 305 with a pattern of bonds as described herein, so as to fastenably engage with areas or patches of hooks 212R attached to or integrally molded on fastening members 120 as described herein. Fastening members 120 may similarly be formed at least in part of a section of web material adapted to serve as loops material 305, so as to fastenably engage with hooks 212F. In this configuration, two pairs of hook-and-loop combinations engage each other to provide benefits associated with combinations of primary and secondary fastening pairs.

Referring to FIG. 13B, it is further contemplated that hooks on fastening members 120 might be omitted entirely, when fastening members 120 are formed of or include loops material such as the section of loops material 305 as described herein. Correspondingly, loops on landing zone 130 may be omitted entirely, and all that is present is section of web material 214 bearing integrally molded areas of hooks 212F. Hooks 212F and loops material of fastening members 120 may be adapted to fastenably engage.

In some embodiments, the backsheet 112 may comprise loop material and integrally molded areas of hooks 212F might be formed directly on, and be integral with, the backsheet 112. In such embodiments, fastening members 120 may include hooks, integrally formed thereon or attached as discrete patches. Likewise, the fastening members 120 may include loop material to engage with the areas of hooks 212F.

Further, referring to FIG. 13C, it is contemplated also that hooks on fastening members 120 might be omitted entirely, when fastening members 120 are formed of or include loops material such as nonwoven web material adapted to serve as loops material as described herein; and a section of web material separate from the backsheet, to be applied to the front waist region, might be omitted. Rather, integrally molded areas of hooks 212F might be formed directly on, and be integral with, component material(s) forming nonwoven web material used as an outer layer for the diaper backsheet 112. Hooks 212F on the front waist region and loops material included with fastening members 120 may be adapted to fastenably engage.

By suitably configuring the hooks-forming cavities in the hooks-forming roller, areas of hooks 212F and 212R may be configured with varying directionality. Some hooks structures in currently marketed hooks materials lack directionality; others have singular directionality or bi-directionality along a single line. Each of FIGS. 14A-16C depicts a front view 220, side view 221 and top view 222 of one of three non-limiting examples of hook shapes, protruding or emerging from a substrate 223. (Substrate 223 may be the material such as a nonwoven web material as described herein, from which the hooks are integrally molded.) Referring to FIGS. 14A-14C, this type of hook shape (sometimes described as a "mushroom" shape) lacks directionality because it is substantially symmetrical about all planes along its vertical (z-direction) axis and/or has substantially similar front and side view profiles. Other types of hook shapes may be formed to have directionality such that they lack such symmetry and/or similarity of front and side views. The hook shape example reflected in FIGS. 15A-15C is substantially unidirectional in that it hooks over predominately in one direction 1HD. The hook shape reflected in FIGS. 16A-16C (sometimes described as an "arrowhead" shape) is substantially bi-directional in that it has two opposing arms 224 that hook over in two opposite directions 2HD.

Returning to FIGS. 12A-E and 13A-C, hooks in areas 212, 212F may be imparted with unidirectionality or bidirectionality along a lateral direction (with respect to a diaper on which the hooks are disposed), or along any direction that is 45 degrees or less from (i.e., approaching) the lateral direction. In a more particular example, hooks in the respective left and right areas 212 and 212F may be imparted with directionality approaching or along the lateral direction and extending toward the longitudinal axis of the diaper. Such directionality provides mechanical structure extending in a direction opposite the ordinary direction of shear forces (directed away from the longitudinal axis in the front region of the diaper) that would be exerted on the hooks in areas 212F while the hooks are engaged with a fastening member 120 while the diaper is being worn. As a result, the fastening strength is increased and/or attachment is more secure, as compared with non-directional hooks of similar size, material utilization (shape volume) and numerical density. In addition, such directionality can reduce skin abrasion caused by contact with hooks as the configuration results in a softer side/surface of the hooks contacting the skin, to the extent contact occurs.

Referring to FIG. 13A, the hooks 212R on fastening member 120 may be imparted with directionality toward the longitudinal axis of the diaper (when the fastening member is in the open position as shown). Such directionality would oppose the ordinary direction of shear forces that would be exerted on the hooks in areas 212F while the hooks are engaged with a fastening member 120 while the diaper is being worn, providing for added fastening strength and/or more secure attachment, as compared with non-directional hooks of similar size, material utilization (shape volume) and numerical density.

In any of the foregoing examples, fastening members 120 may comprise a laminate 311, as shown in FIG. 13B for example. The laminate 311 may be formed of the section of nonwoven web material adapted to serve as loops material 300 as described herein and an elasticizing member 317 such as a layer of elastomeric film, or a plurality of longitudinally spaced, laterally-oriented strands of elastomeric material. The elastomeric member(s) may be joined with the nonwoven loops material while the elastomeric member(s) is(are) in a laterally strained condition, such that the nonwoven loops material forms ruffles or gathers of laterally gathered nonwoven material upon relaxation of the elastomeric member(s) and imparts elastic stretchability to the fastening member when the diaper is donned on a wearer. The laminate may be bonded by ultrasonic bonds, mechanical bonds, adhesive bonds, and any combinations thereof. Alternatively, the elasticized member may be joined to the loops material at zero relative strain and subsequently activated to produce elasticity.

It is also contemplated that loops material may be disposed on a separate substrate from hooks. For example, loops material 300 may be supplied as a separate patch and attached to the chassis, while hooks may be integrally formed from the backsheet.

Hysteresis Test

The following test methods utilize a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23 deg. C.+−2 deg. C. and relative humidity of 50%+−2%. The samples are conditioned for 24 hours prior to testing.

1. Select a 2.54 cm (width), 7.62 cm (length) sample of the material for testing. In some cases, if it is not be possible to get a 2.54 cm×7.62 cm sample, a smaller sample may be used, but a gage length of 25 mm must still be used. If the sample is activated or includes an activation portion, the length of the sample is taken in the direction of activation.

2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

3. Calibrate the tester according to the manufacturer's instructions.

4. Set the distance between the grips at 25 mm.

5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length (lini), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100%.

6(a) First cycle loading: Pull the sample to a strain of 50% at a constant cross head speed of 254 mm/min.

6(b) First cycle unloading: Hold the sample at 50% strain for 30 seconds and then return the crosshead to its starting position (0% strain) at a constant cross head speed of 254 mm/min. Hold the sample in the unstrained state for 1 minute.

6(c) Set from second cycle loading: Pull the sample at a constant cross head speed of 254 mm/min, till it reaches a load of 0.05 N/25.4 mm (0.020 N/cm). Record the extended gauge length (lext). Next, return the crosshead to its starting position (zero strain) at a constant cross head speed of 254 mm/min. Set is defined as the strain at a second cycle load of 0.05 N/25.4 mm (0.020 N/cm). Calculate % set as indicated below.

6(d) Second cycle unload: Next, return the crosshead to its starting position (zero strain) at a constant cross head speed of 254 mm/min.

Percent Set is defined as the percent strain at a second cycle load of 0.05 N/25.4 mm (0.020 N/cm). Calculate % set as indicated below.

A computer data system records the force exerted on the sample during the test as a function of applied strain. From the resulting data generated, the following quantities are reported (note that loads are reported as force divided by the width of the sample and do not take into account the thickness of the sample):

1. Loads at 25% strain and 50% strain (N/cm)
2. % set (Percent Strain measured at a second cycle load of 0.02N/cm);
3. % set=(lext−lini)/lini*100%.

Five repetitions are done on each sample and the average and standard deviation reported.

The Hysteresis Test can be suitably modified depending on the expected attributes and/or properties of the particular material sample to be measured. For example, the Test can be suitably modified where a sample of the length and width specified above are not available from the subject article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or exampled herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended examples all such changes and modifications that are within the scope of this invention.

What is claimed is:

1. A disposable open-form diaper, comprising:
   a chassis comprising a liquid permeable topsheet, a liquid impermeable backsheet and an absorbent core structure disposed between the topsheet and the backsheet; a front waist region; a rear waist region; and a crotch region disposed between the front waist region and the rear waist region; a longitudinal axis and a lateral axis;
   a fastening member joined to the chassis in the rear waist region and extending laterally away from the longitudinal axis, including a first fastening component disposed thereon; and
   a second fastening component disposed on the front waist region;
   wherein one of both of the first and second fastening components comprises a section of nonwoven web material on which an array of hooks is formed, wherein the section of web material comprises filaments of polymeric material;
   the nonwoven web material having a machine direction of formation, the filaments of polymeric material having a machine direction bias and being consolidated and bonded in a pattern of thermal bonds,
   the section of nonwoven web material comprising a section of loops material having a machine direction dimension of at least 20 mm, a cross direction dimension of at least 20 mm, and a surface area of at least 314 mm$^2$, and being bonded in a continuous loops-forming bond, or pattern of discrete loops-forming bonds, wherein:
   any identifiable linear path along the section of loops material that has a width greater than 2 mm and forms an angle of 45 degrees or less with the machine direction (MD) at least partially overlies the loops-forming bond or bonds in the pattern, at a plurality of locations along the path;
   wherein at least some of the hooks are thermally formed at least in part of the polymeric material of the filaments such that at least part of the array is integral with the nonwoven web material;
   wherein when the section of nonwoven web material is deemed to lie along an x-y plane, the hooks are formed to extend in a z-direction with respect to the x-y plane, and hook over along one or more hook directions that cross the machine direction of formation of the web material at an angle of no more than 45 degrees.

2. The diaper of claim 1 wherein a maximum identifiable dimension (PFL) between locations at which the bond or bonds are overlaid by any such path is from 1 mm to 12 mm.

3. The diaper of claim 1 wherein the backsheet comprises the section of nonwoven material.

4. The diaper of claim 1 wherein the section of nonwoven material is discrete from and attached to the backsheet.

5. The diaper of claim 1 wherein at least some of the hooks are thermally formed at least in part of a second polymeric material supplementing the polymeric material of the filaments.

6. The diaper of claim 1 wherein the array of hooks is set back from one or more edges of the section of nonwoven web material.

7. A disposable open-form diaper, comprising:

a chassis comprising a liquid permeable topsheet, a liquid impermeable backsheet and an absorbent core structure disposed between the topsheet and the backsheet; a front waist region; a rear waist region; and a crotch region disposed between the front waist region and the rear waist region; a longitudinal axis and a lateral axis;

a fastening member joined to the chassis in the rear waist region and extending laterally away from the longitudinal axis, including a first fastening component disposed thereon; and a second fastening component disposed on the front waist region;

wherein one of both of the first and second fastening components comprises a section of nonwoven web material on which an array of hooks is formed, wherein the section of web material comprises filaments of polymeric material;

the nonwoven web material having a machine direction of formation, the filaments of polymeric material having a machine direction bias and being consolidated and bonded in a pattern of thermal bonds, the section of nonwoven web material comprising a section of loops material having a machine direction dimension of at least 20 mm, a cross direction dimension of at least 20 mm, and a surface area of at least 314 mm$^2$, and being bonded in a continuous loops-forming bond, or pattern of discrete loops-forming bonds, wherein:

any identifiable linear path along the section of loops material that has a width greater than 2 mm and forms an angle of 45 degrees or less with the machine direction (MD) at least partially overlies the loops-forming bond or bonds in the pattern, at a plurality of locations along the path;

wherein at least some of the hooks are thermally formed at least in part of the polymeric material of the filaments such that at least part of the array is integral with the nonwoven web material;

wherein when the section of nonwoven web material is deemed to lie along an x-y plane, the hooks are formed to extend in a z-direction with respect to the x-y plane, and the hooks comprise a first plurality of hooks that hook over in a first direction and a second plurality of hooks that hook over in a direction differing from the first direction.

8. The diaper of claim 7 wherein a maximum identifiable dimension (PFL) between locations at which the bond or bonds are overlaid by any such path is from 1 mm to 12 mm.

9. The diaper of claim 7 wherein the backsheet comprises the section of nonwoven material.

10. The diaper of claim 7 wherein the section of nonwoven material is discrete from and attached to the backsheet.

11. The diaper of claim 7 wherein at least some of the hooks are thermally formed at least in part of a second polymeric material supplementing the polymeric material of the filaments.

12. The diaper of claim 7 wherein the section of nonwoven web material is disposed on the front waist region, the first plurality of hooks is disposed on the web material proximate a left side of the front waist region, and the second plurality of hooks is disposed on the web material proximate a right side of the front waist region.

13. The diaper of claim 7 wherein the array of hooks is set back from one or more edges of the section of nonwoven web material.

* * * * *